(12) United States Patent
Sakaida

(10) Patent No.: US 6,792,070 B2
(45) Date of Patent: Sep. 14, 2004

(54) RADIATION IMAGE RECORDING METHOD AND APPARATUS

(75) Inventor: Hideyuki Sakaida, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 29 days.

(21) Appl. No.: 10/270,289

(22) Filed: Oct. 15, 2002

(65) Prior Publication Data

US 2003/0072414 A1 Apr. 17, 2003

(30) Foreign Application Priority Data

Oct. 16, 2001 (JP) ........................................ 2001-318263
Oct. 16, 2001 (JP) ........................................ 2001-318265

(51) Int. Cl.[7] .............................................. G01N 23/04
(52) U.S. Cl. ........................................ 378/62; 378/98.8
(58) Field of Search ....................... 378/62, 98.2–98.12

(56) References Cited

U.S. PATENT DOCUMENTS 5,802,137 A * 9/1998 Wilkins ......................... 378/85
6,493,422 B2 * 12/2002 Wilkins et al. ............. 378/98.9
6,600,807 B2 * 7/2003 Sakaida ......................... 378/62

FOREIGN PATENT DOCUMENTS

JP 2000-245721 9/2000

OTHER PUBLICATIONS

SPIE, vol. 3154, 1997, pp. 72.
J. Phys. D: Appl. Phys. 32, 1999, A145–A151.

* cited by examiner

Primary Examiner—Craig E. Church
Assistant Examiner—Jurie Yun
(74) Attorney, Agent, or Firm—Sughrue Mion, PLLC

(57) ABSTRACT

Radiation is irradiated to an object, and the radiation, which carries image information of the object, is detected at a plurality of positions for image recording, which are set at different distances from the object, a plurality of radiation images of the object being thereby acquired. The acquisition of the radiation images is performed by use of a plurality of two-dimensional detectors, such that the radiation, which carries the image information of the object, at a position for image recording, which is remote from the object, is detected with a two-dimensional detector having a sensitivity higher than the sensitivity of a two-dimensional detector for detecting the radiation at a position for image recording, which is close to the object.

21 Claims, 14 Drawing Sheets

RADIATION IMAGE RECORDING METHOD AND APPARATUS

BACKGROUND OF THE INVENTION

1. Field of the Invention

This invention relates to a radiation image recording method and apparatus. This invention particularly relates to a radiation image recording method and apparatus suitable for operations, wherein radiation carrying image information of an object is detected at a plurality of positions for image recording, which are set at different distances from the object, a plurality of radiation images being thereby obtained, and a phase contrast image is formed by use of the plurality of the radiation images.

2. Description of the Related Art

Radiation image recording and reproducing techniques have heretofore been used in practice. With the radiation image recording and reproducing techniques, radiation is irradiated to an object, and the radiation carrying image information of the object is detected with a two-dimensional detector, such as a stimulable phosphor sheet or a radiation detecting panel comprising a plurality of detecting devices arrayed in two-dimensional directions. In this manner, an image signal representing a radiation image of the object is obtained. The image signal is then subjected to various types of image processing, and the processed image signal is utilized for reproducing the radiation image as a visible image.

With the radiation image recording and reproducing techniques utilizing the stimulable phosphor sheet, the radiation image of the object is stored on the stimulable phosphor sheet comprising a layer of a stimulable phosphor, and the stimulable phosphor sheet, on which the radiation image has been stored, is exposed to stimulating rays, such as a laser beam, which cause the stimulable phosphor sheet to emit light in proportion to the amount of energy stored thereon during its exposure to radiation. The light emitted by the stimulable phosphor sheet is photoelectrically detected, and the image signal representing the radiation image of the object is thereby obtained. With the radiation image recording and reproducing techniques utilizing the radiation detecting panel comprising the plurality of the detecting devices arrayed in two-dimensional directions, an electric signal component corresponding to a radiation dose delivered to each of the detecting devices is formed by each of the detecting devices, and the image signal representing the radiation image of the object is obtained from the thus formed electric signal components.

In the radiation image obtained in the manner described above, a difference in intensity of radiation having passed through the object is illustrated as the image. For example, in cases where the radiation image of an object comprising a bone and a soft tissue is recorded, the radiation having passed through the bone attenuates largely, and the dose of the radiation, which has passed through the bone and is delivered to the detector, becomes small. However, the radiation having passed through the soft tissue does not much attenuate, and the dose of the radiation, which has passed through the soft tissue and is delivered to the detector, becomes comparatively large. Therefore, in the cases of the object comprising the bone and the soft tissue, a radiation image comprising a bone pattern having a low image density and a soft tissue pattern having a high image density, in which the contrast between the bone pattern and the soft tissue pattern is high, i.e. in which the quantity of information is large, is obtained.

However, in cases where the object is mainly constituted of soft tissues alone as in the cases of the radiation image for a diagnosis of mammary cancer, the difference in amount of attenuation of radiation between the soft tissues is not very large. Therefore, in such cases, a radiation image, in which the contrast between the soft tissue patterns is low, i.e. in which the quantity of information is small, is obtained.

Accordingly, phase contrast imaging techniques for visualizing a phase difference of radiation occurring due to the passage of the radiation through an object have been proposed. As in the cases of light, the radiation is an electromagnetic wave and travels and propagates as the wave. The recording of the object image with the phase contrast imaging techniques is based upon the phenomenon such that, in cases where the radiation is irradiated to two different substances, the phase of the wave of the radiation varies before the radiation passes through the substances and after the radiation has passed through the substances due to a difference in how the radiation propagates through the substances, and a phase difference is thereby caused to occur. In cases where the object is constituted of the soft tissues, the phase difference of the radiation becomes larger than the difference in amount of attenuation of radiation. Therefore, in such cases, the image recording may be performed with the phase contrast imaging techniques, and the phase difference of the radiation may be illustrated as a phase contrast image. In this manner, a fine difference between the soft tissues is capable of being visualized.

The phase contrast imaging techniques are described in detail in, for example, "Quantitative aspects of coherent hard X-ray imaging: Talbot image and holographic reconstruction" by Peter Cloetens, et al., Proc, SPIE, Vol. 3154 (1997), pp. 72–82 (hereinbelow referred to as Literature 1); and "Hard X-ray phase imaging using simple propagation of a coherent synchrotron radiation beam" by Peter Cloetens, et al., J. Phys. D: Appl. Phys. 32 (1999), pp. A145–A151 (hereinbelow referred to as Literature 2). Literature 1 and Literature 2 show that, in cases where an image recording operation is performed by use of two-dimensional detectors, such as radiation detecting panels, at a plurality of positions for image recording, which are set at different distances from the object, a plurality of image signals respectively representing a plurality of radiation images of the object are thereby obtained, and operation processing with predetermined algorithms is performed on the plurality of the image signals, a phase contrast image is capable of being formed.

In cases where a radiation image is obtained, the radiation dose delivered to a two-dimensional detector varies in inverse proportion to the square of the distance between a radiation source and the two-dimensional detector. Also, the radiation propagates in a divergent form from the radiation source, and therefore the size of the radiation image detected by a two-dimensional detector, which is located at a long distance from the object, becomes large. Accordingly, a radiation imaging apparatus, wherein a read-out gain at the time of image readout of a radiation image is adjusted in accordance with the distance between an object and a two-dimensional detector, or a magnification ratio of the radiation image is calculated in accordance with the distance between the object and the two-dimensional detector, has been proposed in, for example, Japanese Unexamined Patent Publication No. 2000-245721.

Further, a technique, wherein image size enlargement or reduction processing or image density transform processing is performed on a plurality of radiation images, which are obtained at a plurality of positions for image recording, such that a phase contrast image is capable of being obtained accurately, has been proposed in, for example, Japanese Patent Application No. 2001-146138.

However, with the techniques, wherein the read-out gain is adjusted, or the image density is transformed, a long time is required to perform the read-out gain adjustment or the image density transform, and radiation images cannot be detected efficiently.

SUMMARY OF THE INVENTION

The primary object of the present invention is to provide a radiation image recording method, wherein radiation is capable of being detected efficiently, and a phase contrast image is capable of being formed accurately.

Another object of the present invention is to provide a radiation image recording method, wherein a plurality of radiation images, from which a phase contrast image is to be formed, are capable of being acquired efficiently.

The specific object of the present invention is to provide an apparatus for carrying out the radiation image recording method.

The present invention provides a first radiation image recording method, comprising the steps of:

i) irradiating radiation to an object, and
ii) detecting the radiation, which carries image information of the object, at a plurality of positions for image recording, which are set at different distances from the object, a plurality of radiation images of the object being thereby acquired, wherein the acquisition of the plurality of the radiation images of the object is performed by use of a plurality of two-dimensional detectors, such that the radiation, which carries the image information of the object, at a position for image recording, which is remote from the object, is detected with a two-dimensional detector having a sensitivity higher than the sensitivity of a two-dimensional detector for detecting the radiation at a position for image recording, which is close to the object.

As the content of a phosphor in a two-dimensional detector becomes high, the sensitivity of the two-dimensional detector becomes high. Therefore, in the first radiation image recording method in accordance with the present invention, the radiation, which carries the image information of the object, at the position for image recording, which is remote from the object, may be detected with a two-dimensional detector having a phosphor content higher than the phosphor content of a two-dimensional detector for detecting the radiation at the position for image recording, which is close to the object. In this manner, as the position for image recording becomes remote from the object, the sensitivity of the two-dimensional detector is capable of being set to be high.

Also, as the content of the phosphor in the two-dimensional detector becomes high, the thickness of the phosphor becomes large, and the transmittance with respect to the radiation becomes low. Further, the two-dimensional detector located at the position for image recording, which is close to the object, need not necessarily have a high sensitivity, and the radiation at the position for image recording, which is close to the object, is capable of being detected accurately with the two-dimensional detector having a comparatively low sensitivity. Therefore, the first radiation image recording method in accordance with the present invention should preferably be modified such that a two-dimensional detector for detecting the radiation at a position for image recording, which is close to the object, comprises a phosphor having a thickness smaller than the thickness of the phosphor of a two-dimensional detector for detecting the radiation at a position for image recording, which is remote from the object. Specifically, the first radiation image recording method in accordance with the present invention should preferably be modified such that a two-dimensional detector for detecting the radiation at a position for image recording, which is close to the object, has a radiation transmittance higher than the radiation transmittance of a two-dimensional detector for detecting the radiation at a position for image recording, which is remote from the object.

Also, the first radiation image recording method in accordance with the present invention should preferably be modified such that a phase contrast image is formed from the plurality of the radiation images.

The present invention also provides a first radiation image recording apparatus for carrying out the first radiation image recording method in accordance with the present invention. Specifically, the present invention also provides a first radiation image recording apparatus, comprising:

a plurality of two-dimensional detectors, each of the two-dimensional detectors being located at one of a plurality of positions for image recording, which are set at different distances from an object, in order to detect radiation, which carries image information of the object, at the one position for image recording, the plurality of the two-dimensional detectors being set such that a two-dimensional detector located at a position for image recording, which is remote from the object, has a sensitivity higher than the sensitivity of a two-dimensional detector located at a position for image recording, which is close to the object, wherein the radiation, which carries the image information of the object, is detected with the plurality of the two-dimensional detectors at the plurality of the positions for image recording, a plurality of radiation images of the object being thereby acquired.

The first radiation image recording apparatus in accordance with the present invention should preferably be modified such that the plurality of the two-dimensional detectors are set such that a two-dimensional detector located at a position for image recording, which is close to the object, has a radiation transmittance higher than the radiation transmittance of a two-dimensional detector located at a position for image recording, which is remote from the object.

Also, the first radiation image recording apparatus in accordance with the present invention should preferably be modified such that the apparatus further comprises image forming means for forming a phase contrast image from the plurality of the radiation images.

The present invention further provides a second radiation image recording apparatus for carrying out the first radiation image recording method in accordance with the present invention. Specifically, the present invention further provides a second radiation image recording apparatus, comprising:

i) a plurality of image recording units located successively along a direction of an optical axis of radiation, which carries image information of an object, each of the image recording units comprising:

a two-dimensional detector for detecting the radiation, which carries the image information of the object, movement means for moving the two-dimensional detector in the direction of the optical axis of the radiation, and a plurality of position sensors, each of the position sensors detecting arrival of the two-dimensional detector at one of a plurality of positions for image recording, which have been predetermined on a movement path of the two-dimensional detector moved by the movement means, and ii) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording, wherein a plurality of the two-dimensional detectors of the plurality of the image recording units are set such that a two-dimensional detector of an image recording unit, which is located at a position remote from the object, has a sensitivity higher than the sensitivity of a two-dimensional detector of an image recording unit, which is located at a position close to the object.

The second radiation image recording apparatus in accordance with the present invention may be modified such that the apparatus comprises a plurality of reading means, each of which is located for one of the plurality of the image recording units. In such cases, the operations for acquiring the radiation images by use of the plurality of the image recording unit are capable of being performed simultaneously. As a result, the operations for acquiring the radiation images at all of the positions for image recording are capable of being performed efficiently.

Also, the second radiation image recording apparatus in accordance with the present invention may be modified such that the plurality of the two-dimensional detectors of the plurality of the image recording units are set such that a two-dimensional detector of an image recording unit, which is located at a position close to the object, has a radiation transmittance higher than the radiation transmittance of a two-dimensional detector of an image recording unit, which is located at a position remote from the object.

Further, the second radiation image recording apparatus in accordance with the present invention may be modified such that the apparatus further comprises image forming means for forming a phase contrast image from the plurality of the radiation images.

The present invention still further provides a second radiation image recording method, comprising the steps of:

i) irradiating radiation to an object, and ii) detecting the radiation, which carries image information of the object, at a plurality of positions for image recording, which are set at different distances from the object, a plurality of radiation images of the object being thereby acquired, wherein the acquisition of the plurality of the radiation images of the object is performed such that a resolution of a radiation image acquired at a position for image recording, which is remote from the object, becomes higher than the resolution of a radiation image acquired at a position for image recording, which is close to the object.

The second radiation image recording method in accordance with the present invention may be modified such that the acquisition of the plurality of the radiation images of the object is performed by use of a plurality of two-dimensional detectors, such that the radiation, which carries the image information of the object, at a position for image recording, which is remote from the object, is detected with a two-dimensional detector having a resolution higher than the resolution of a two-dimensional detector for detecting the radiation at a position for image recording, which is close to the object.

In order for the resolution of the two-dimensional detector to be set to be high, a light receiving area of each of the detecting devices constituting the two-dimensional detector may be set to be small, and the detecting devices may be arrayed at a high density.

Also, the second radiation image recording method in accordance with the present invention may be modified such that the acquisition of the plurality of the radiation images of the object is performed by use of at least one two-dimensional detector, such that a rate of thinning-out of signal reading from the two-dimensional detector at the time of the acquisition of a radiation image at a position for image recording, which is remote from the object, is lower than the rate of thinning-out of the signal reading from the two-dimensional detector at the time of the acquisition of a radiation image at a position for image recording, which is close to the object.

In the aforesaid modification of the second radiation image recording method in accordance with the present invention, the rate of thinning-out of the signal reading from the two-dimensional detector at the time of the acquisition of the radiation image at the position for image recording, which is remote from the object, is set to be lower than the rate of thinning-out of the signal reading from the two-dimensional detector at the time of the acquisition of the radiation image at the position for image recording, which is close to the object. Specifically, the signal reading from the two-dimensional detector may be thinned out such that a signal component is read from only one detecting device, which is among a plurality of detecting devices adjacent to one another in the two-dimensional detector, and the thus read signal component is taken as each of pixel values in the radiation image, which pixel values correspond to the plurality of the detecting devices adjacent to one another. In such cases, at the time of the acquisition of the radiation image at the position for image recording, which is close to the object, the rate of thinning-out of the signal reading from the two-dimensional detector is set to be high, and a signal component is thus read from only one detecting device, which is among a large number of detecting devices adjacent to one another. Also, at the time of the acquisition of the radiation image at the position for image recording, which is remote from the object, the number of the detecting devices adjacent to one another, from which only one signal component is read, is set to be small, and the rate of thinning-out of the signal reading is thus set to be low.

Further, the second radiation image recording method in accordance with the present invention may be modified such that a phase contrast image is formed from the plurality of the radiation images.

The present invention also provides a third radiation image recording apparatus for carrying out the second radiation image recording method in accordance with the present invention. Specifically, the present invention also provides a third radiation image recording apparatus, comprising:

a plurality of two-dimensional detectors, each of the two-dimensional detectors being located at one of a plurality of positions for image recording, which are set at different distances from an object, in order to detect radiation, which carries image information of the object, at the one position for image recording, the plurality of the two-dimensional detectors being set such that a two-dimensional detector located at a position for image recording, which is remote from the object, has a resolution higher than the resolution of a two-dimensional detector located at a position for image recording, which is close to the object, wherein the radiation, which carries the image information of the object, is detected with the plurality of the two-dimensional detectors at the plurality of the positions for image recording, a plurality of radiation images of the object being thereby acquired.

The third radiation image recording apparatus in accordance with the present invention may be modified such that the apparatus further comprises image forming means for forming a phase contrast image from the plurality of the radiation images.

The present invention further provides a fourth radiation image recording apparatus for carrying out the second radiation image recording method in accordance with the present invention. Specifically, the present invention further provides a fourth radiation image recording apparatus, comprising:

i) a plurality of image recording units located successively along a direction of an optical axis of radiation, which carries image information of an object, each of the image recording units comprising:
   a two-dimensional detector for detecting the radiation, which carries the image information of the object,
   movement means for moving the two-dimensional detector in the direction of the optical axis of the radiation, and
   a plurality of position sensors, each of the position sensors detecting arrival of the two-dimensional detector at one of a plurality of positions for image recording, which have been predetermined on a movement path of the two-dimensional detector moved by the movement means, and ii) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording, wherein a plurality of the two-dimensional detectors of the plurality of the image recording units are set such that a two-dimensional detector of an image recording unit, which is located at a position remote from the object, has a resolution higher than the resolution of a two-dimensional detector of an image recording unit, which is located at a position close to the object.

The fourth radiation image recording apparatus in accordance with the present invention may be modified such that the apparatus comprises a plurality of reading means, each of which is located for one of the plurality of the image recording units. In such cases, the operations for acquiring the radiation images by use of the plurality of the image recording unit are capable of being performed simultaneously. As a result, the operations for acquiring the radiation images at all of the positions for image recording are capable of being performed efficiently.

Also, the fourth radiation image recording apparatus in accordance with the present invention may be modified such that the apparatus further comprises image forming means for forming a phase contrast image from the plurality of the radiation images.

The present invention still further provides a fifth radiation image recording apparatus for carrying out the second radiation image recording method in accordance with the present invention. Specifically, the present invention still further provides a fifth radiation image recording apparatus, comprising:

i) at least one two-dimensional detector for detecting radiation, which carries image information of an object, ii) movement means for moving the two-dimensional detector in a direction of an optical axis of the radiation, iii) a plurality of position sensors, each of the position sensors detecting arrival of the two-dimensional detector at one of a plurality of positions for image recording, which have been predetermined on a movement path of the two-dimensional detector moved by the movement means, and iv) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording, the reading means performing the reading of signals from the two-dimensional detector such that a rate of thinning-out of signal reading from the two-dimensional detector at the time of the acquisition of a radiation image at a position for image recording, which is remote from the object, is lower than the rate of thinning-out of the signal reading from the two-dimensional detector at the time of the acquisition of a radiation image at a position for image recording, which is close to the object.

The fifth radiation image recording apparatus in accordance with the present invention may be modified such that the apparatus further comprises image forming means for forming a phase contrast image from the plurality of the radiation images.

With the first radiation image recording method in accordance with the present invention and the first and second radiation image recording apparatuses in accordance with the present invention, the acquisition of the plurality of the radiation images of the object is performed by use of the plurality of the two-dimensional detectors, such that the radiation, which carries the image information of the object, at the position for image recording, which is remote from the object, is detected with a two-dimensional detector having a sensitivity higher than the sensitivity of a two-dimensional detector for detecting the radiation at the position for image recording, which is close to the object. Therefore, as in the cases of the two-dimensional detector located at the position for image recording, which is close to the object, the radiation is capable of being detected accurately with the two-dimensional detector located at the position for image recording, which is remote from the object. Accordingly, the image densities of the plurality of the radiation images acquired in this manner are capable of being kept to be approximately identical. As a result, the phase contrast image is capable of being formed accurately from the plurality of the radiation images. Also, particular operations for adjusting the read-out gains of the two-dimensional detectors or adjusting the image densities of the acquired radiation images need not be performed, and therefore the radiation images, which are capable of yielding the accurate phase contrast image, are capable of being acquired efficiently.

With the second radiation image recording method in accordance with the present invention and the third, fourth, and fifth radiation image recording apparatuses in accordance with the present invention, the acquisition of the plurality of the radiation images of the object is performed such that the resolution of the radiation image acquired at the position for image recording, which is remote from the object, becomes higher than the resolution of the radiation image acquired at the position for image recording, which is close to the object. Therefore, the acquisition of the radiation images is capable of being performed such that high-frequency information due to a diffraction image, which information occurs to a high extent at the position for image recording remote from the object, may not be lost. Also, at the position for image recording, which is close to the object, a radiation image having a resolution lower than the resolution of the radiation image acquired at the position for image recording, which is remote from the object, is obtained. Accordingly, the signal reading from the two-dimensional detector is capable of being performed efficiently. As a result, the plurality of the radiation images, from which the phase contrast image is to be formed, are capable of being acquired efficiently.

DESCRIPTION OF THE PREFERRED EMBODIMENTS

The present invention will hereinbelow be described in further detail with reference to the accompanying drawings.

Figure 1:
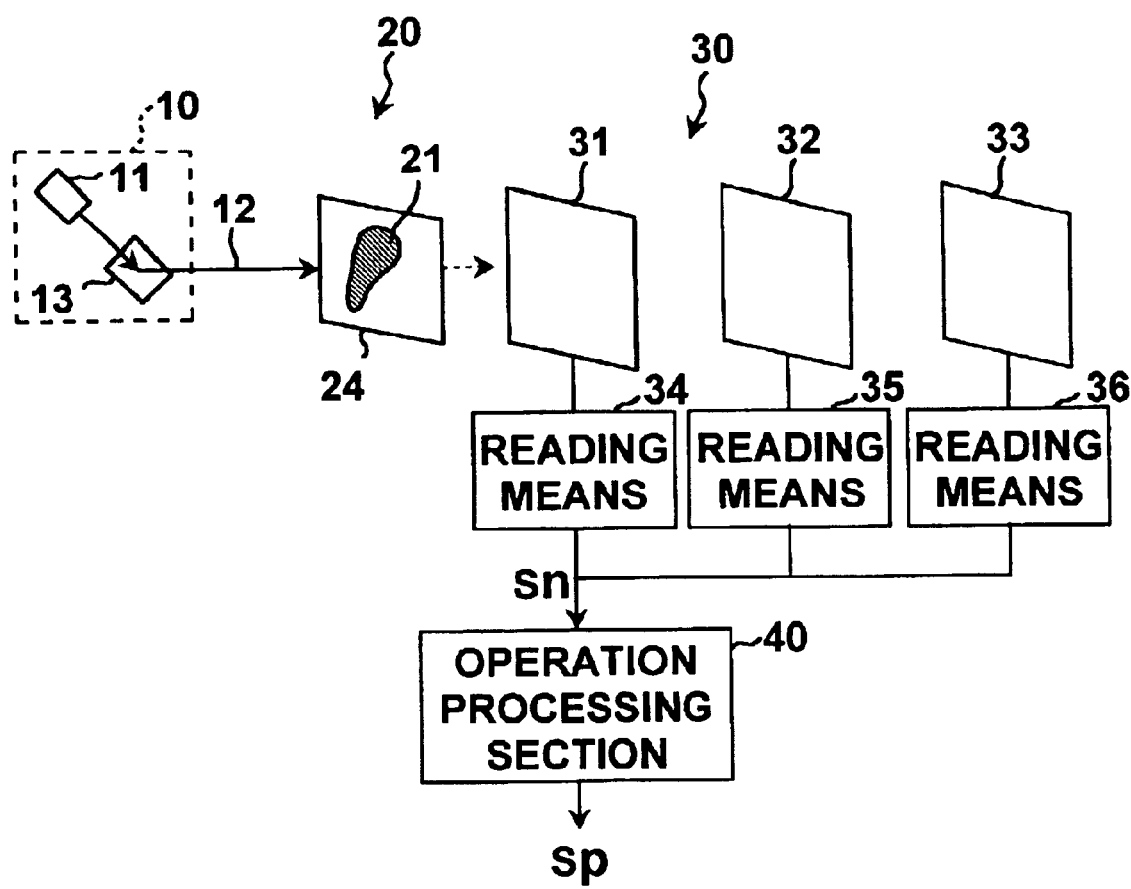
FIG. 1 is a schematic block diagram showing a phase contrast imaging apparatus, in which a first embodiment of the radiation image recording apparatus in accordance with the present invention is employed.

FIG. 1 is a schematic block diagram showing a phase contrast imaging apparatus, in which a first embodiment of the radiation image recording apparatus in accordance with the present invention is employed.

As illustrated in FIG. 1, the first embodiment of the radiation image recording apparatus in accordance with the present invention comprises an X-ray source 10 for producing X-rays and irradiating the X-rays to an object 21, and an object support section 20 for supporting the object 21. The radiation image recording apparatus also comprises a recording section 30 for detecting the X-rays, which carry image information of the object 21, and obtaining image signals Sn, where n=1 to N, each of which represents one of a plurality of X-ray images of the object 21. The radiation image recording apparatus further comprises an operation processing section 40 for forming an image signal Sp, which represents a phase contrast image, from the plurality of the image signals Sn.

The X-ray source 10 comprises an X-ray beam producing device 11, which produces a synchrotron radiation beam, and a crystal 13, which may be a silicon crystal and converts the synchrotron radiation beam into monochromatic X-rays (hereinbelow referred to simply as the X-rays) 12. The synchrotron radiation beam, which has been produced by the X-ray beam producing device 11, is reflected from the crystal 13, and the monochromatic X-rays 12 are thereby obtained.

The object support section 20 is provided with a support base 24 for supporting the object 21.

The recording section 30 is provided with a plurality of (in this case, three) X-ray detecting panels 31, 32, and 33, each of which is located at one of a plurality of predetermined positions for image recording. Each of the X-ray detecting panels 31, 32, and 33 comprises a phosphor and a plurality of detecting devices arrayed in two-dimensional directions. The recording section 30 is also provided with reading means 34, 35, and 36. The reading means 34 reads electric signal components from the plurality of the detecting devices constituting the X-ray detecting panel 31 in order to obtain one of the plurality of the image signals Sn. The reading means 35 reads the electric signal components from the plurality of the detecting devices constituting the X-ray detecting panel 32 in order to obtain one of the plurality of the image signals Sn. The reading means 36 reads the electric signal components from the plurality of the detecting devices constituting the X-ray detecting panel 33 in order to obtain one of the plurality of the image signals Sn. In lieu of the plurality of the reading means being utilized, the recording section 30 may be provided with only one reading means, which is capable of successively reading the electric signal components from the X-ray detecting panels 31, 32, and 33.

Figure 2:
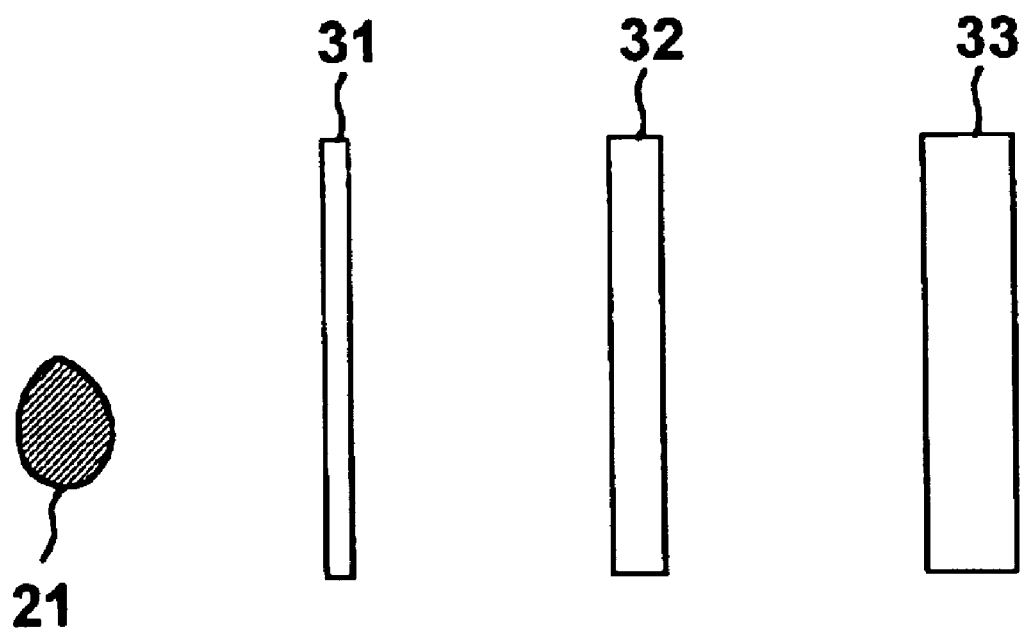
FIG. 2 is an explanatory view showing thicknesses of radiation detecting panels.

In cases where the image recording operation is performed by use of the plurality of the X-ray detecting panels 31, 32, and 33 as in the first embodiment, as the distance between the position for image recording and the object 21 becomes long, the X-ray dose delivered to the X-ray detecting panel located at the position for image recording becomes small, and the diffraction quantity of the X-rays 12 delivered to the X-ray detecting panel located at the position for image recording becomes large. Therefore, in the first embodiment, the X-ray detecting panels 31, 32, and 33 are set such that the X-ray detecting panel located at the position for image recording, which is remote from the object 21, has a sensitivity higher than the sensitivity of the X-ray detecting panel located at the position for image recording, which is close to the object 21. Specifically, as illustrated in FIG. 2, the X-ray detecting panels 31, 32, and 33 are set such that the thickness of the phosphor of the X-ray detecting panel located at the position for image recording, which is remote from the object 21, is larger than the thickness of the phosphor of the X-ray detecting panel located at the position for image recording, which is close to the object 21, such that the phosphor content becomes higher than the phosphor content in the X-ray detecting panel located at the position for image recording, which is close to the object 21. Accordingly, at the position for image recording, which is remote from the object 21, as in the cases of the position for image recording, which is close to the object 21, the X-rays 12 are capable of being detected accurately. Also, at the position for image recording, which is remote from the object 21, a diffraction image is capable of being detected accurately.

In this embodiment, as described above, the thickness of the phosphor of the X-ray detecting panel located at the position for image recording, which is close to the object 21, is smaller than the thickness of the phosphor of the X-ray detecting panel located at the position for image recording, which is remote from the object 21. Therefore, the degree of attenuation of the X-rays 12 impinging upon the X-ray detecting panel located at the position for image recording, which is remote from the object 21, is capable of being kept low.

The operation processing section 40 performs image size reduction processing on the X-ray images, which are represented by the image signals Sn obtained from the X-ray detecting panels 31, 32, and 33, such that the sizes of the X-ray images represented by the image signals Sn become identical with the size of the X-ray image represented by an image signal S1 obtained from the position for image recording, which is closest to the object 21. Also, the operation processing section 40 forms the image signal Sp, which represents the phase contrast image, from the image signals Sn, which have been obtained from the image size reduction processing.

Specifically, in cases where the image recording operation is performed by use of the plurality of the X-ray detecting panels 31, 32, and 33 as in the first embodiment, as the distance between the position for image recording and the object 21 becomes long, the size of the X-ray image obtained at the position for image recording becomes large. Therefore, in the first embodiment, the sizes of the X-ray images represented by the image signals Sn are corrected in accordance with the distances between the positions for image recording and the object 21. More specifically, in cases where a magnification ratio of an X-ray image, which is obtained at one of the positions for image recording other than the position for image recording closest to the object 21, to the X-ray image, which is obtained at the position for image recording closest to the object 21, is equal to M (where M>1), the image size reduction processing is performed such that the X-ray image, which is obtained at one of the positions for image recording other than the position for image recording closest to the object 21, may be reduced to a size 1/M times as large as the original size.

In cases where the size of the X-ray image obtained from the X-ray detecting panel located at the position for image recording, which is remote from the object 21, becomes large at the time of the image recording operation, the dose of the X-rays 12 delivered to the X-ray detecting panel per unit area of the X-ray detecting panel becomes small. In order for the decrease in X-ray dose to be compensated for, an image signal component representing each of pixels in the X-ray image may be multiplied by $1/M^2$. In this manner, the decrease in X-ray dose due to the magnification of the X-ray image maybe compensated for.

Also, in accordance with the technique described in Literature 1 mentioned above, the image signal Sp representing the phase contrast image is formed from the image signals Sn, which have been obtained from the image size reduction processing described above. The technique described in Literature 1 will be described hereinbelow. Specifically, the transmittance of the object 21 with respect to the X-rays 12 may be represented by Formula (1) shown below.

$$T(x, y) = A(x, y)e^{i\psi(x, y)} \quad (1)$$

wherein T(x, y) represents the transmittance function, A(x, y) represents the transmittance intensity function, $\psi(x, y)$ represents the phase shift quantity function, and (x, y) represents the coordinate values representing the position on the X-ray detecting panel.

In cases where the object 21 is a thin body such that the transmittance intensity is negligible, i.e. A(x, y) is close to 1, as represented by Formula (2) shown below, frequency components of the phase shift quantity are capable of being calculated from frequency components $I_{dn}(fx, fy)$, which are obtained from Fourier transform of images $I_{dn}(x, y)$ recorded with the X-ray detecting panels 31, 32, and 33 located at distances dn (where n=1 to N) from the object 21.

The relationship between the X-ray dose delivered to each of the X-ray detecting panels 31, 32, and 33 and the value of each of the pixels in the X-ray image represented by each of the image signals Sn is capable of being detected previously. Therefore, conversion tables for converting the values of the pixels in the X-ray images, which are represented by the image signals Sn, into the X-ray dose values maybe prepared from the relationships between the X-ray doses delivered to the X-ray detecting panels 31, 32, and 33 and the values of the pixels in the X-ray images represented by the image signals Sn. Reference may be made to the conversion tables, and the images $I_{dn}(x, y)$ are thus capable of being formed from the values of the pixels at the positions (x, y) on the images represented by the image signals Sn, which have been acquired at the distances dn.

$$\psi(fx, fy \neq 0) = \frac{\sum_{n=1\wedge N} \exp(i\pi\lambda dnf^2) Idn(fx, fy)}{N - \sum_{n=1\wedge N} \exp(2i\pi\lambda dnf^2)} \quad (2)$$

wherein N represents the number of the image signals Sn, f represents the frequency, $\psi$(fx, fy≠0) represents the frequency component of the phase shift quantity at the time at which the frequency is not equal to 0, and $I_{dn}$(fx, fy) represents the frequency component of $I_{dn}$(x, y).

Also, the frequency components of the phase shift quantities may be subjected to inverse Fourier transform, and the phase shift quantities, i.e. phase differences, $\psi$(x, y) are thereby capable of being calculated. The phase differences $\psi$(x, y) take values falling within the range of 0 to $2\pi$. Therefore, the calculated phase differences $\psi$(x, y) may be allocated to, for example, 8-bit values. In this manner, the image signal Sp representing the phase contrast image is capable of being obtained.

In the foregoing, it is assumed that the transmittance intensity is negligible, i.e. A(x, y) is close to 1. As for thick bodies, the phase shift quantity is capable of being calculated by use of the same algorithms as those described above.

How the first embodiment of the radiation image recording apparatus in accordance with the present invention operates will be described hereinbelow.

Figure 3:
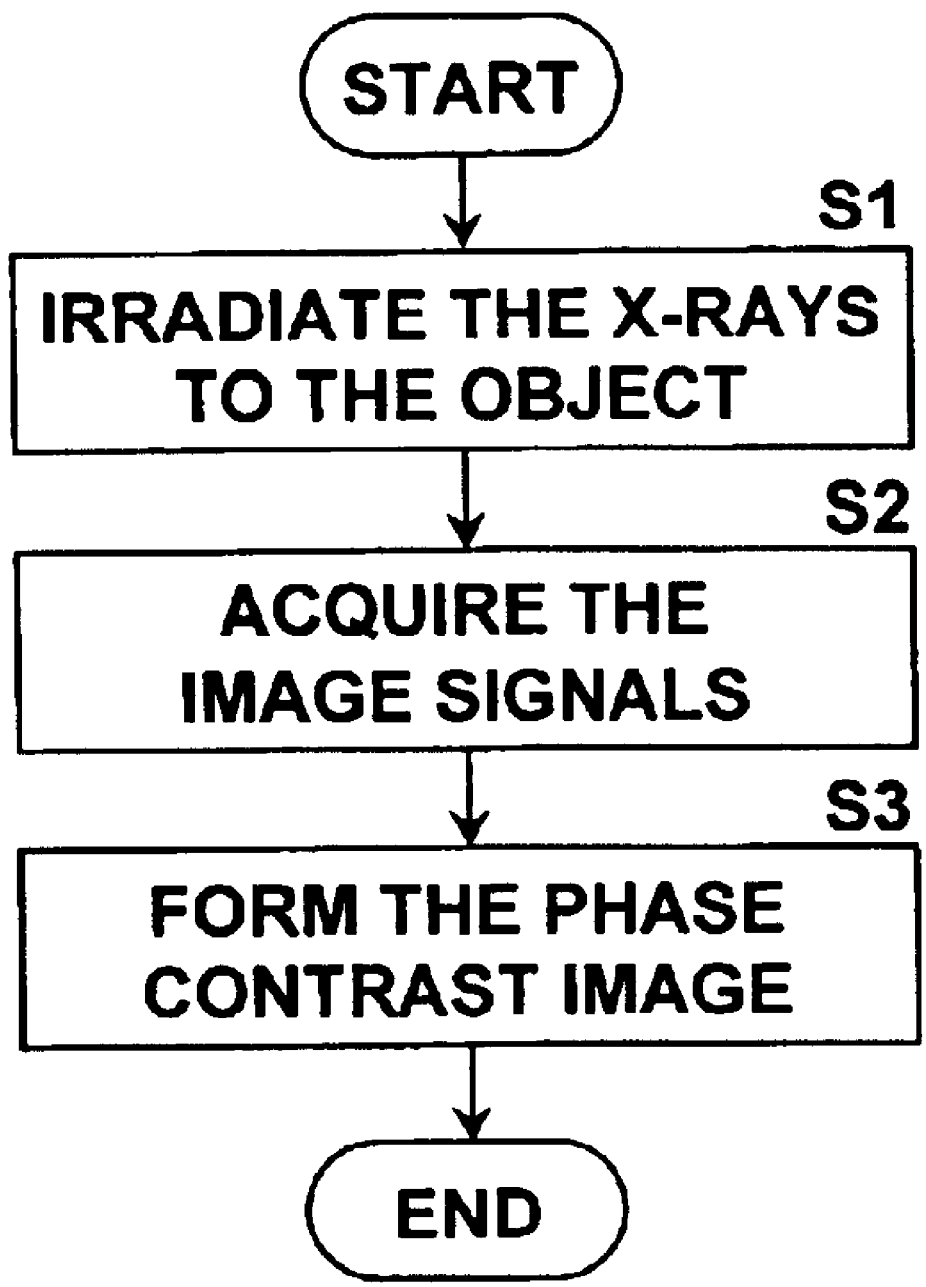
FIG. 3 is a flow chart showing how the first embodiment of the radiation image recording apparatus in accordance with the present invention operates.

FIG. 3 is a flow chart showing how the first embodiment of the radiation image recording apparatus in accordance with the present invention operates. As illustrated in FIG. 3, firstly, in a step S1, the X-ray beam producing device 11 is actuated to produce the synchrotron radiation beam, and the synchrotron radiation beam is reflected from the crystal 13. In this manner, the monochromatic X-rays 12 are radiated out from the X-ray source 10 and irradiated to the object 21. Also, in a step S2, the electric signal components are read out from the plurality of the detecting devices, which constitute each of the X-ray detecting panels 31, 32, and 33, and with each of the reading means 34, 35, and 36 located at the plurality of the positions for image recording. In this manner, the image signals Sn, each of which represents one of the X-ray images obtained at the plurality of the positions for image recording, are acquired.

In a step S3, the thus acquired image signals Sn are fed into the operation processing section 40. In the operation processing section 40, the image signals Sn are subjected to the image size reduction processing. Also, in the manner described above, the image signal Sp representing the phase contrast image is formed from the image signals Sn, which have been obtained from the image size reduction processing. At this stage, the processing with the radiation image recording apparatus is finished. The image signal Sp representing the phase contrast image may be utilized for the reproduction of a visible image on a monitor or for the print outputting with a printer.

As described above, in the first embodiment, the X-ray images are acquired by use of the X-ray detecting panels 31, 32, and 33 having been set such that the X-ray detecting panel located at the position for image recording, which is remote from the object 21, has a sensitivity higher than the sensitivity of the X-ray detecting panel located at the position for image recording, which is close to the object 21. Therefore, as in the cases of the X-ray detecting panel 31 located at the position for image recording, which is close to the object 21, the X-rays 12 are capable of being detected accurately with the X-ray detecting panel 33 located at the position for image recording, which is remote from the object 21. Accordingly, the image densities of the plurality of the X-ray images acquired in this manner are capable of being kept to be approximately identical. As a result, the image signal Sp representing the phase contrast image is capable of being formed accurately from the plurality of the X-ray images. Also, particular operations for adjusting the read-out gains of the X-ray detecting panels 31, 32, and 33 or adjusting the image densities of the acquired X-ray images need not be performed, and therefore the X-ray images, which are capable of yielding the accurate phase contrast image, are capable of being acquired efficiently.

A second embodiment of the radiation image recording apparatus in accordance with the present invention will be described hereinbelow.

Figure 4:
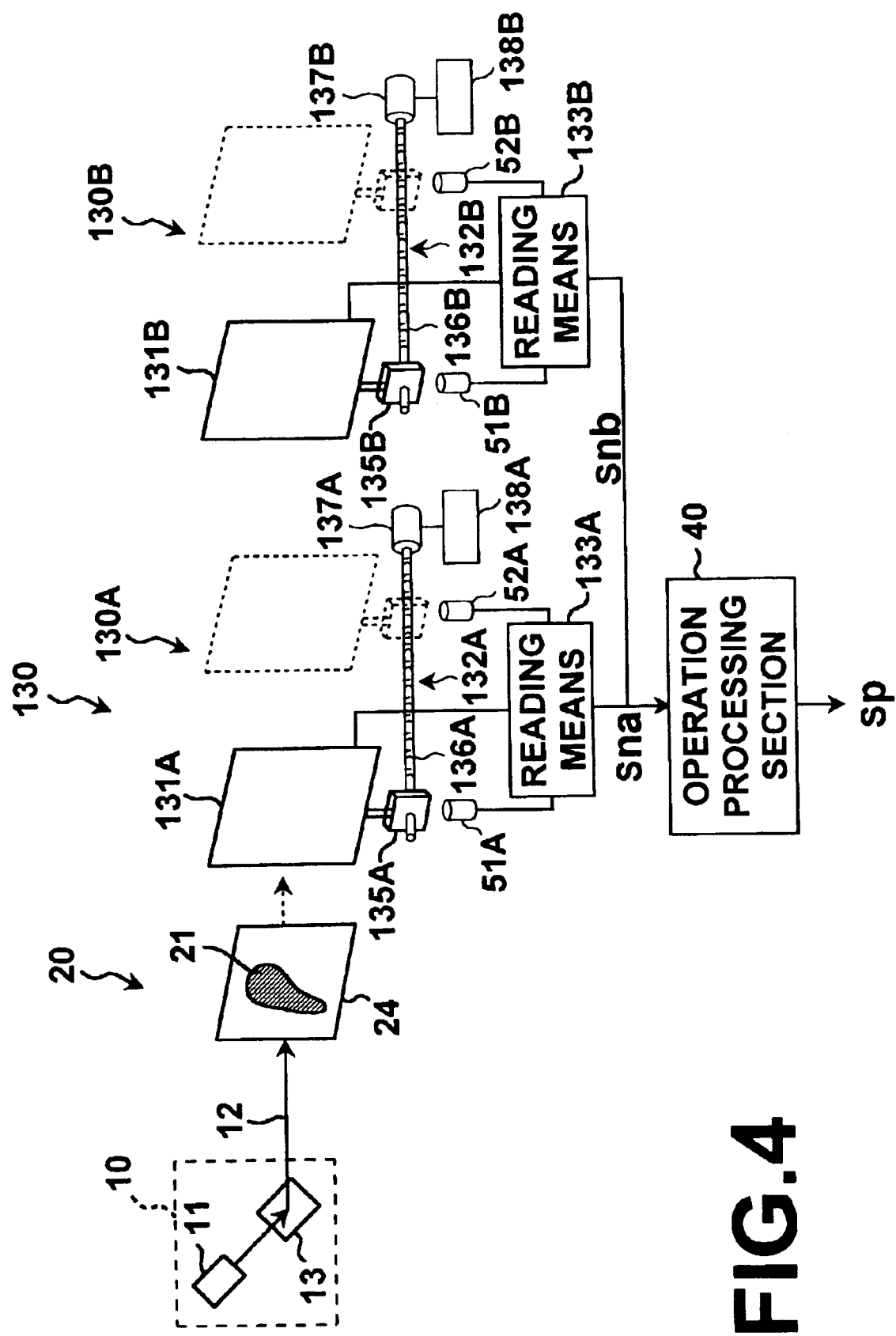
FIG. 4 is a schematic block diagram showing a phase contrast imaging apparatus, in which a second embodiment of the radiation image recording apparatus in accordance with the present invention is employed.

FIG. 4 is a schematic block diagram showing a phase contrast imaging apparatus, in which the second embodiment of the radiation image recording apparatus in accordance with the present invention is employed. In FIG. 4, similar elements are numbered with the same reference numerals with respect to FIG. 1. The second embodiment is constituted basically in the same manner as that for the first embodiment, except for the recording section.

In the second embodiment, a recording section 130 comprises a first image recording unit 130A and a second image recording unit 130B.

The first image recording unit 130A is provided with an X-ray detecting panel 131A, which comprises a phosphor and a plurality of detecting devices arrayed in two-dimensional directions. The first image recording unit 130A is also provided with movement means 132A for moving the X-ray detecting panel 131A in parallel with the direction along which the X-rays 12 carrying the image information of the object 21 travels. The first image recording unit 130A is further provided with reading means 133A for reading electric signal components from the plurality of the detecting devices, which constitute the X-ray detecting panel 131A, at each of a plurality of positions for image recording, which have been set previously on the movement path of the X-ray detecting panel 131A. The reading means 133A thus obtains each of a plurality of image signals Sna, which represent the X-ray images recorded at the plurality of the positions for image recording.

Also, the second image recording unit 130B is provided with an X-ray detecting panel 131B, which comprises a phosphor and a plurality of detecting devices arrayed in two-dimensional directions. The second image recording unit 130B is also provided with movement means 132B for moving the X-ray detecting panel 131B in parallel with the direction along which the X-rays 12 carrying the image information of the object 21 travels. The second image recording unit 130B is further provided with reading means 133B for reading electric signal components from the plurality of the detecting devices, which constitute the X-ray detecting panel 131B, at each of a plurality of positions for image recording, which have been set previously on the movement path of the X-ray detecting panel 131B. The reading means 133B thus obtains each of a plurality of image signals Snb, which represent the X-ray images recorded at the plurality of the positions for image recording.

The movement means 132A is provided with a support member 135A, which supports the X-ray detecting panel 131A and has an internal thread section. The movement means 132A is also provided with a screw rod 136A extending in parallel with the direction along which the X-rays 12 travels. The screw rod 136A has external threads for engagement with the internal thread section of the support member 135A. The movement means 132A is further provided with a motor 137A for rotating the screw rod 136A around a rotation axis extending in the direction along which the X-rays 12 travels. The movement means 132A is still further provided with a control section 138A for controlling the operation of the motor 137A. The motor 137A is actuated by the control section 138A in order to rotate the screw rod 136A. In accordance with the direction of rotation of the screw rod 136A, the support member 135A is moved in a direction heading towards the object 21 or in a direction heading away from the object 21. As a result, the X-ray detecting panel 131A is moved in a direction heading towards the object 21 or in a direction heading away from the object 21.

Also, the movement means 132B is provided with a support member 135B, which supports the X-ray detecting panel 131B and has an internal thread section. The movement means 132B is also provided with a screw rod 136B extending in parallel with the direction along which the X-rays 12 travels. The screw rod 136B has external threads for engagement with the internal thread section of the support member 135B. The movement means 132B is further provided with a motor 137B for rotating the screw rod 136B around a rotation axis extending in the direction along which the X-rays 12 travels. The movement means 132B is still further provided with a control section 138B for controlling the operation of the motor 137B. The motor 137B is actuated by the control section 138B in order to rotate the screw rod 136B. In accordance with the direction of rotation of the screw rod 136B, the support member 135B is moved in a direction heading towards the object 21 or in a direction heading away from the object 21. As a result, the X-ray detecting panel 131B is moved in a direction heading towards the object 21 or in a direction heading away from the object 21.

Further, each of position sensors 51A and 52A is located at one of the positions for image recording in the first image recording unit 130A. Each of the position sensors 51A and 52A detects the arrival of the X-ray detecting panel 131A, which is moved by the movement means 132A, at the corresponding position for image recording. At the time at which the X-ray detecting panel 131A arrives at the corresponding position for image recording, each of the position sensors 51A and 52A outputs a detection signal. The detection signal is fed into the reading means 133A. In accordance with the detection signal, the reading means 133A reads the electric signal components from the plurality of the detecting devices, which constitute the X-ray detecting panel 131A, in order to obtain an image signal Sna, which represents the X-ray image recorded at the position for image recording described above.

Also, each of position sensors 51B and 52B is located at one of the positions for image recording in the second image recording unit 130B. Each of the position sensors 51B and 52B detects the arrival of the X-ray detecting panel 131B, which is moved by the movement means 132B, at the corresponding position for image recording. At the time at which the X-ray detecting panel 131B arrives at the corresponding position for image recording, each of the position sensors 51B and 52B outputs a detection signal. The detection signal is fed into the reading means 133B. In accordance with the detection signal, the reading means 133B reads the electric signal components from the plurality of the detecting devices, which constitute the X-ray detecting panel 131B, in order to obtain an image signal Snb, which represents the X-ray image recorded at the position for image recording described above.

In the second embodiment, the position sensors 51A and 52A are located at the two positions in the first image recording unit 130A. Also, the position sensors 51B and 52B are located at the two positions in the second image recording unit 130B. Therefore, four image signals Sn (i.e., image signals S1, S2, S3, and S4) are obtained respectively from the four positions for image recording.

Also, in the second embodiment, the X-ray detecting panel 131A and the X-ray detecting panel 131B are set such that the sensitivity of the X-ray detecting panel 131B, which constitutes the second image recording unit 130B located on the side remote from the object 21, is higher than the sensitivity of the X-ray detecting panel 131A, which constitutes the first image recording unit 130A located on the side close to the object 21. Specifically, the thickness of the phosphor of the X-ray detecting panel 131B is set to be larger than the thickness of the phosphor of the X-ray detecting panel 131A. In this manner, the content of the phosphor in the X-ray detecting panel 131B is set to be higher than the content of the phosphor in the X-ray detecting panel 131A. Therefore, at the position for image recording, which is remote from the object 21, as in the cases of the position for image recording, which is close to the object 21, the X-rays 12 are capable of being detected accurately. Also, at the position for image recording, which is remote from the object 21, a diffraction image is capable of being detected accurately.

In the same manner as that for the first embodiment described above, the operation processing section 40 performs the image size reduction processing on the X-ray images, which are represented by the image signals Sn, such that the sizes of the X-ray images represented by the image signals Sn become identical with the size of the X-ray image represented by the image signal S1 obtained from the position for image recording, which is closest to the object 21. Also, the operation processing section 40 forms the image signal Sp, which represents the phase contrast image, from the image signals Sn, which have been obtained from the image size reduction processing.

How the second embodiment of the radiation image recording apparatus in accordance with the present invention operates will be described hereinbelow.

Figure 5:
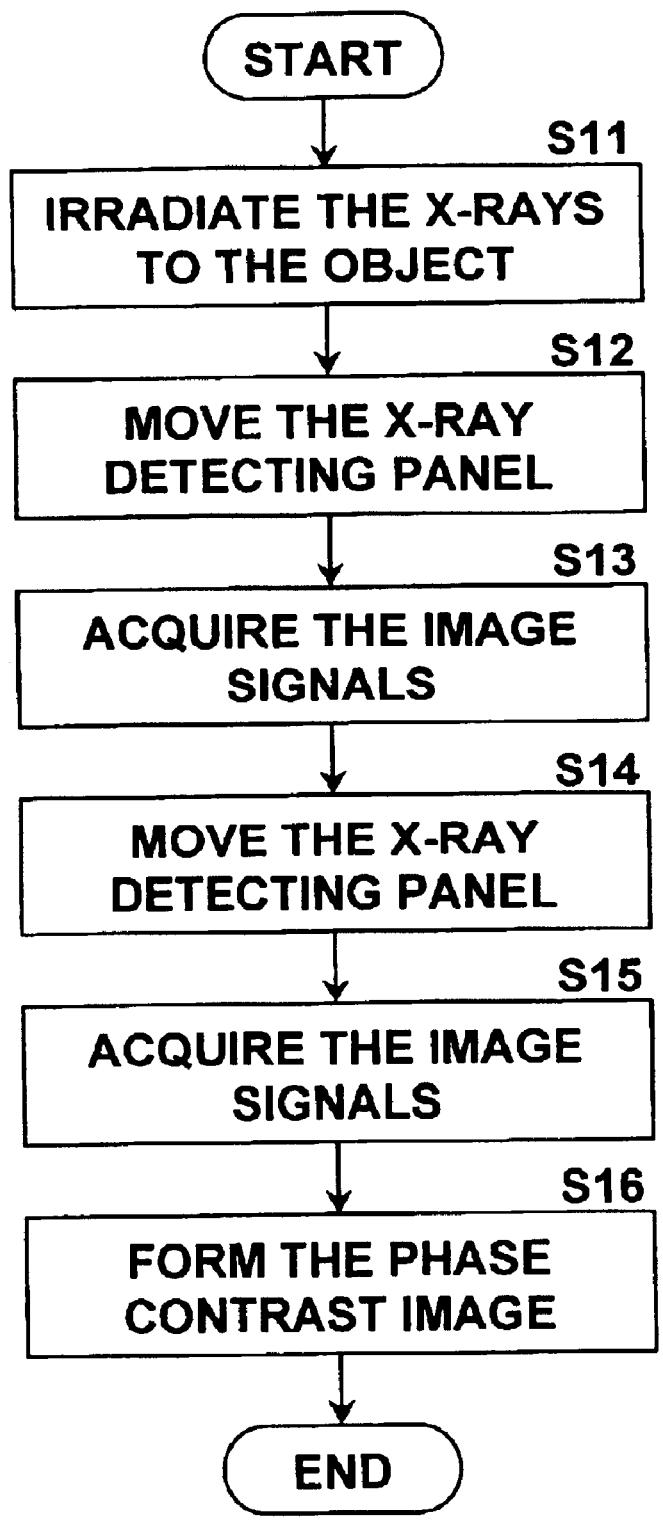
FIG. 5 is a flow chart showing how the second embodiment of the radiation image recording apparatus in accordance with the present invention operates.

FIG. 5 is a flow chart showing how the second embodiment of the radiation image recording apparatus in accordance with the present invention operates. As illustrated in FIG. 5, firstly, in a step S11, the X-ray beam producing device 11 is actuated to produce the synchrotron radiation beam, and the synchrotron radiation beam is reflected from the crystal 13. In this manner, the monochromatic X-rays 12 are radiated out from the X-ray source 10 and irradiated to the object 21. At the same time, an image recording operation is performed with the first image recording unit 130A. Specifically, in a step S12, the motor 137A is actuated by the control section 138A, and the X-ray detecting panel 131A is moved in the direction heading away from an initial position, which is closest to the object 21. Also, in a step S13, with the timing with which the detection signal is fed from each of the position sensors 51A and 52A into the reading means 133A during the movement of the X-ray detecting panel 131A, the electric signal components are read out from the plurality of the detecting devices, which constitute the X-ray detecting panel 131A, and with the reading means 133A. In this manner, the image signals Sna, each of which represents one of the X-ray images obtained at the positions for image recording, are acquired.

After the image recording operation has been performed at the position for image recording, which is remotest from the object 21, in the first image recording unit 130A, an image recording operation is performed with the second image recording unit 130B. Specifically, in a step S14, the motor 137B is actuated by the control section 138B, and the X-ray detecting panel 131B is moved in the direction heading away from an initial position, which is closest to the object 21. Also, in a step S15, with the timing with which the detection signal is fed from each of the position sensors 51B and 52B into the reading means 133B during the movement of the X-ray detecting panel 131B, the electric signal components are read out from the plurality of the detecting devices, which constitute the X-ray detecting panel 131B, and with the reading means 133B. In this manner, the image signals Snb, each of which represents one of the X-ray images obtained at the positions for image recording, are acquired.

In a step S16, the thus acquired image signals Sna and Snb are fed into the operation processing section 40. In the operation processing section 40, in the same manner as that for the first embodiment described above, the image signal Sp representing the phase contrast image is formed from the image signals Sna and Snb. At this stage, the processing with the radiation image recording apparatus is finished. The image signal Sp representing the phase contrast image may be utilized for the reproduction of a visible image on a monitor or for the print outputting with a printer.

In the second embodiment described above, after the image recording operation has been performed with the first image recording unit 130A, the image recording operation with the second image recording unit 130B is performed. Alternatively, both the image recording operation with the first image recording unit 130A and the image recording operation with the second image recording unit 130B may be performed simultaneously.

Also, in the second embodiment described above, the two image recording units 130A and 130B are utilized. Alternatively, at least three image recording units may be utilized. In such cases, the X-ray detecting panels of the image recording units are set such that an X-ray detecting panel of an image recording unit located on the side remote from the object 21 has a sensitivity higher than the sensitivity of an X-ray detecting panel of an image recording unit located on the side close to the object 21.

In the first and second embodiments described above, the X-ray detecting panels are set such that the X-ray detecting panel for detecting the X-rays 12 at the position for image recording, which is remote from the object 21, has a sensitivity higher than the sensitivity of the X-ray detecting panel for detecting the X-rays 12 at the position for image recording, which is close to the object 21. Further, the sensitivity of a certain X-ray detecting panel may be set also in accordance with the number of the X-ray detecting panels, which are closer to the object 21 than the certain X-ray detecting panel is.

Figure 6:
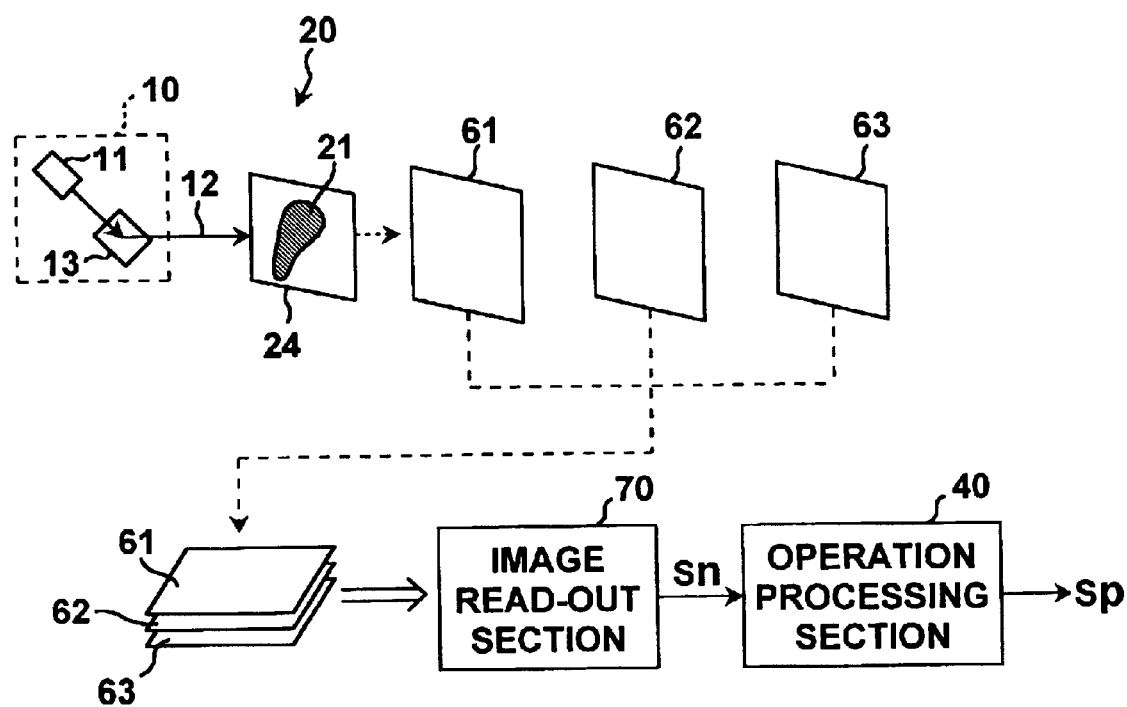
FIG. 6 is a schematic block diagram showing a phase contrast imaging apparatus, in which a third embodiment of the radiation image recording apparatus in accordance with the present invention is employed.

In the first embodiment described above, the X-ray images are acquired with the X-ray detecting panels 31, 32, and 33. Alternatively, as in a third embodiment shown in FIG. 6, in lieu of the X-ray detecting panels 31, 32, and 33, a plurality of (in this case, three) stimulable phosphor sheets 61, 62, and 63 may be utilized. In this case, the stimulable phosphor sheets 61, 62, and 63 may be set such that a stimulable phosphor sheet located at the position for image recording, which is remote from the object 21, comprises a phosphor thicker than a phosphor of a stimulable phosphor sheet located at the position for image recording, which is close to the object 21. In this manner, the stimulable phosphor sheets 61, 62, and 63 may be set such that the stimulable phosphor sheet located at the position for image recording, which is remote from the object 21, has a sensitivity higher than the sensitivity of the stimulable phosphor sheet located at the position for image recording, which is close to the object 21.

In cases where the X-ray images have been recorded on the stimulable phosphor sheets 61, 62, and 63, each of the stimulable phosphor sheets 61, 62, and 63, on which the X-ray images have been stored, is sent to an image read-out section 70. In the image read-out section 70, each of the stimulable phosphor sheets 61, 62, and 63, on which the X-ray images have been stored, is exposed to stimulating rays, which cause the stimulable phosphor sheet to emit light in proportion to the amount of energy stored thereon during its exposure to the X-rays 12. Also, the light emitted by each of the stimulable phosphor sheets 61, 62, and 63 is photoelectrically detected. In this manner, the plurality of the image signals Sn, each of which represents one of the X-ray images having been stored on the stimulable phosphor sheets 61, 62, and 63, are obtained. In the same manner as that for the first embodiment described above, the thus obtained image signals Sn are fed into the operation processing section 40. In the operation processing section 40, the image signal Sp representing the phase contrast image is formed from the image signals Sn.

Fourth, fifth, sixth, and seventh embodiments of the radiation image recording apparatus in accordance with the present invention will be described hereinbelow.

Figure 7:
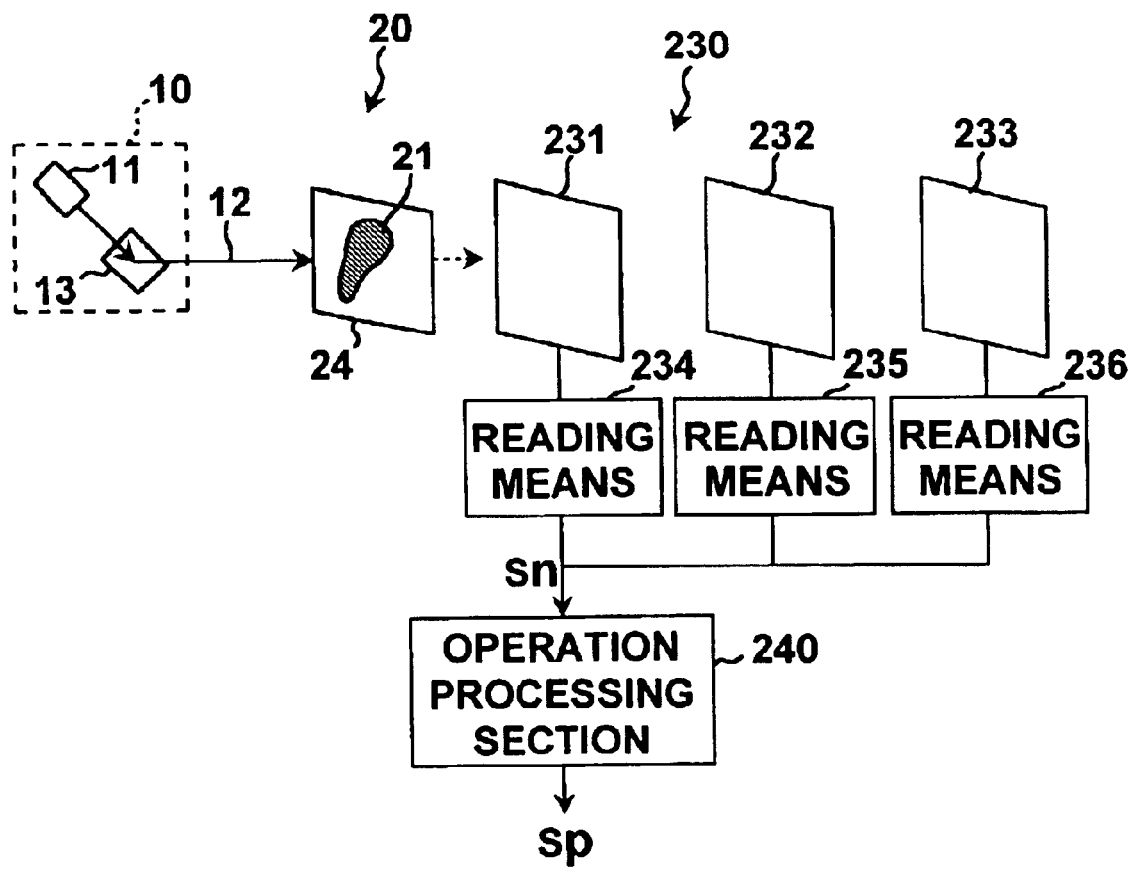
FIG. 7 is a schematic block diagram showing a phase contrast imaging apparatus, in which a fourth embodiment of the radiation image recording apparatus in accordance with the present invention is employed.

FIG. 7 is a schematic block diagram showing a phase contrast imaging apparatus, in which a fourth embodiment of the radiation image recording apparatus in accordance with the present invention is employed.

As illustrated in FIG. 7, the fourth embodiment of the radiation image recording apparatus in accordance with the present invention comprises the X-ray source 10 for producing X-rays and irradiating the X-rays to the object 21, and the object support section 20 for supporting the object 21. The radiation image recording apparatus also comprises a recording section 230 for detecting the X-rays, which carry the image information of the object 21, and obtaining the image signals Sn, where n=1 to N, each of which represents one of a plurality of X-ray images of the object 21. The radiation image recording apparatus further comprises an operation processing section 240 for forming the image signal Sp, which represents the phase contrast image, from the plurality of the image signals Sn.

The X-ray source 10 comprises the X-ray beam producing device 11, which produces the synchrotron radiation beam, and the crystal 13, which may be a silicon crystal and converts the synchrotron radiation beam into the monochromatic X-rays (hereinbelow referred to simply as the X-rays) 12. The synchrotron radiation beam, which has been produced by the X-ray beam producing device 11, is reflected from the crystal 13, and the monochromatic X-rays 12 are thereby obtained.

The object support section 20 is provided with the support base 24 for supporting the object 21.

The recording section 230 is provided with a plurality of (in this case, three) X-ray detecting panels 231, 232, and 233, each of which is located at one of a plurality of predetermined positions for image recording. Each of the X-ray detecting panels 231, 232, and 233 comprises a phosphor and a plurality of detecting devices arrayed in two-dimensional directions. The recording section 230 is also provided with reading means 234, 235, and 236. The reading means 234 reads electric signal components from the plurality of the detecting devices constituting the X-ray detecting panel 231 in order to obtain one of the plurality of the image signals Sn. The reading means 235 reads the electric signal components from the plurality of the detecting devices constituting the X-ray detecting panel 232 in order to obtain one of the plurality of the image signals Sn. The reading means 236 reads the electric signal components from the plurality of the detecting devices constituting the X-ray detecting panel 233 in order to obtain one of the plurality of the image signals Sn. In lieu of the plurality of the reading means being utilized, the recording section 230 may be provided with only one reading means, which is capable of successively reading the electric signal components from the X-ray detecting panels 231, 232, and 233.

In cases where the image recording operation is performed by use of the plurality of the X-ray detecting panels 231, 232, and 233 as in the fourth embodiment, as the distance between the position for image recording and the object 21 becomes long, the diffraction quantity of the X-rays 12 delivered to the X-ray detecting panel located at the position for image recording becomes large. As a result, a large amount of high-frequency information due to a diffraction image is contained in the X-ray image, which is formed at the position for image recording. Also, an X-ray detecting panel having a high resolution is capable of detecting more of the high-frequency information than an X-ray detecting panel having a low resolution. Therefore, in cases where an X-ray detecting panel having a high resolution is utilized, an image signal Sn representing a radiation image is capable of being acquired such that the high-frequency information may not be lost. However, an X-ray image formed at a position for image recording, which is close to the object 21, does not contain a large amount of high-frequency information. Therefore, if an X-ray detecting panel having a high resolution is utilized at the position for image recording, which is close to the object 21, the problems will occur in that, though it is sufficient for an X-ray image, which does not contain a large amount of high-frequency information, to be acquired at the position for image recording, a long time is required to read the signal components from the detecting devices constituting the X-ray detecting panel.

Figure 8:
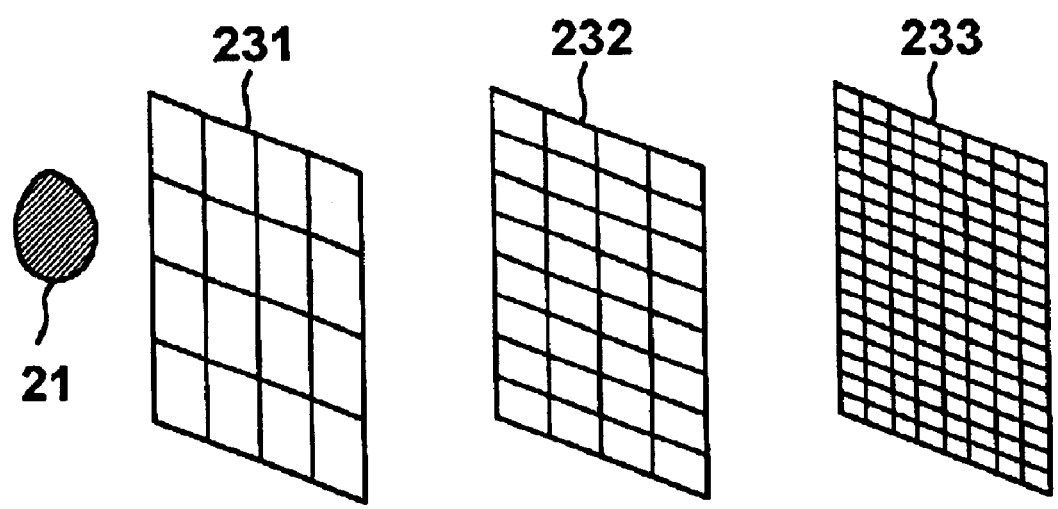
FIG. 8 is an explanatory view showing arraying densities of detecting devices constituting radiation detecting panels.

Therefore, in the fourth embodiment, the X-ray detecting panels 231, 232, and 233 are set such that the X-ray detecting panel located at the position for image recording, which is remote from the object 21, has a resolution higher than the resolution of the X-ray detecting panel located at the position for image recording, which is close to the object 21. Specifically, as illustrated in FIG. 8, the X-ray detecting panels 231, 232, and 233 are set such that the light receiving area of each of the detecting devices constituting the X-ray detecting panel located at the position for image recording, which is remote from the object 21, is smaller than the light receiving area of each of the detecting devices constituting the X-ray detecting panel located at the position for image recording, which is close to the object 21, and the detecting devices constituting the X-ray detecting panel located at the position for image recording, which is remote from the object 21, are arrayed at an array density higher than the array density of the detecting devices constituting the X-ray detecting panel located at the position for image recording, which is close to the object 21. In this manner, the resolution of the X-ray detecting panel located at the position for image recording, which is remote from the object 21, is set to be higher than the resolution of the X-ray detecting panel located at the position for image recording, which is close to the object 21. Accordingly, at the position for image recording, which is remote from the object 21, the high-frequency information due to the diffraction image is capable of being detected accurately.

The operation processing section 240 compensates for differences among resolutions of the X-ray images, which are represented by the image signals Sn obtained from the X-ray detecting panels 231, 232, and 233. Also, the operation processing section 240 performs image size enlargement processing on the X-ray images, which are represented by the image signals Sn obtained from the X-ray detecting panels 231, 232, and 233, such that the sizes of the X-ray images represented by the image signals Sn become identical with the size of the X-ray image represented by an image signal S3 obtained from the position for image recording, which is remotest from the object 21. Further, the operation processing section 240 forms the image signal Sp, which represents the phase contrast image, from the image signals Sn, which have been obtained from the image size enlargement processing.

Specifically, in cases where the resolutions of the X-ray detecting panels 231, 232, and 233 are different from one another as in the fourth embodiment, it is necessary for the resolutions of the X-ray images represented by the image signals Sn to be matched with one another at the time of the formation of the image signal Sp representing the phase contrast image. Therefore, in the fourth embodiment, a compensation is made such that the resolutions of the X-ray images, which are represented by the image signals S1 and S2 having been obtained respectively from the X-ray detecting panels 231 and 232, become identical with the resolution of the X-ray image, which is represented by the image signal S3 having been obtained from the X-ray detecting panel 233 that has the highest resolution among the resolutions of the X-ray detecting panels 231, 232, and 233. In cases where the compensation is made in the manner described above, the problems are capable of being prevented from occurring in that the information of the X-ray image having the highest resolution among the resolutions of the acquired X-ray images is lost.

Also, in cases where the image recording operation is performed by use of the plurality of the X-ray detecting panels 231, 232, and 233 as in the fourth embodiment, as the distance between the position for image recording and the object 21 becomes long, the size of the X-ray image obtained at the position for image recording becomes large. Therefore, in the fourth embodiment, the sizes of the X-ray images represented by the image signals Sn (which have been obtained from the compensation for the resolution) are corrected in accordance with the distances between the positions for image recording and the object 21. More specifically, in cases where the magnification ratio of an X-ray image, which is obtained at one of the positions for image recording other than the position for image recording remotest from the object 21, to the X-ray image, which is obtained at the position for image recording remotest from the object 21, is equal to M (where M<1), the image size enlargement processing is performed such that the X-ray image, which is obtained at one of the positions for image recording other than the position for image recording remotest from the object 21, may be enlarged to a size 1/M times as large as the original size. In this manner, the sizes of the X-ray images, which are obtained at the positions for image recording other than the position for image recording remotest from the object 21, are matched with the size of the X-ray image, which is obtained at the position for image recording remotest from the object 21. In such cases, as in the cases of the resolution described above, the problems are capable of being prevented from occurring in that the information of the X-ray image having the highest resolution among the resolutions of the acquired X-ray images is lost.

In cases where the size of the X-ray image obtained from the X-ray detecting panel located at the position for image recording, which is remote from the object 21, becomes large at the time of the image recording operation, the dose of the X-rays 12 delivered to the X-ray detecting panel per unit area of the X-ray detecting panel becomes small. In order for the decrease in X-ray dose to be compensated for, in cases where the magnification ratio at the position for image recording with respect to the position of the object 21 is represented by L, an image signal component representing each of pixels in the X-ray image may be multiplied by $1/L^2$. In this manner, the decrease in X-ray dose due to the magnification of the X-ray image may be compensated for.

Also, in accordance with the technique described in Literature 1 mentioned above, the image signal Sp representing the phase contrast image is formed from the image signals Sn, which have been obtained from the image size enlargement processing described above.

In the fourth embodiment described above, the sizes of the X-ray images, which are obtained at the positions for image recording other than the position for image recording remotest from the object 21, are enlarged so as to match with the size of the X-ray image, which is obtained at the position for image recording remotest from the object 21. Therefore, when necessary, an image size reduction processing may be performed on the phase contrast image, such that the phase contrast image may have a desired size.

How the fourth embodiment of the radiation image recording apparatus in accordance with the present invention operates will be described hereinbelow.

Figure 9:
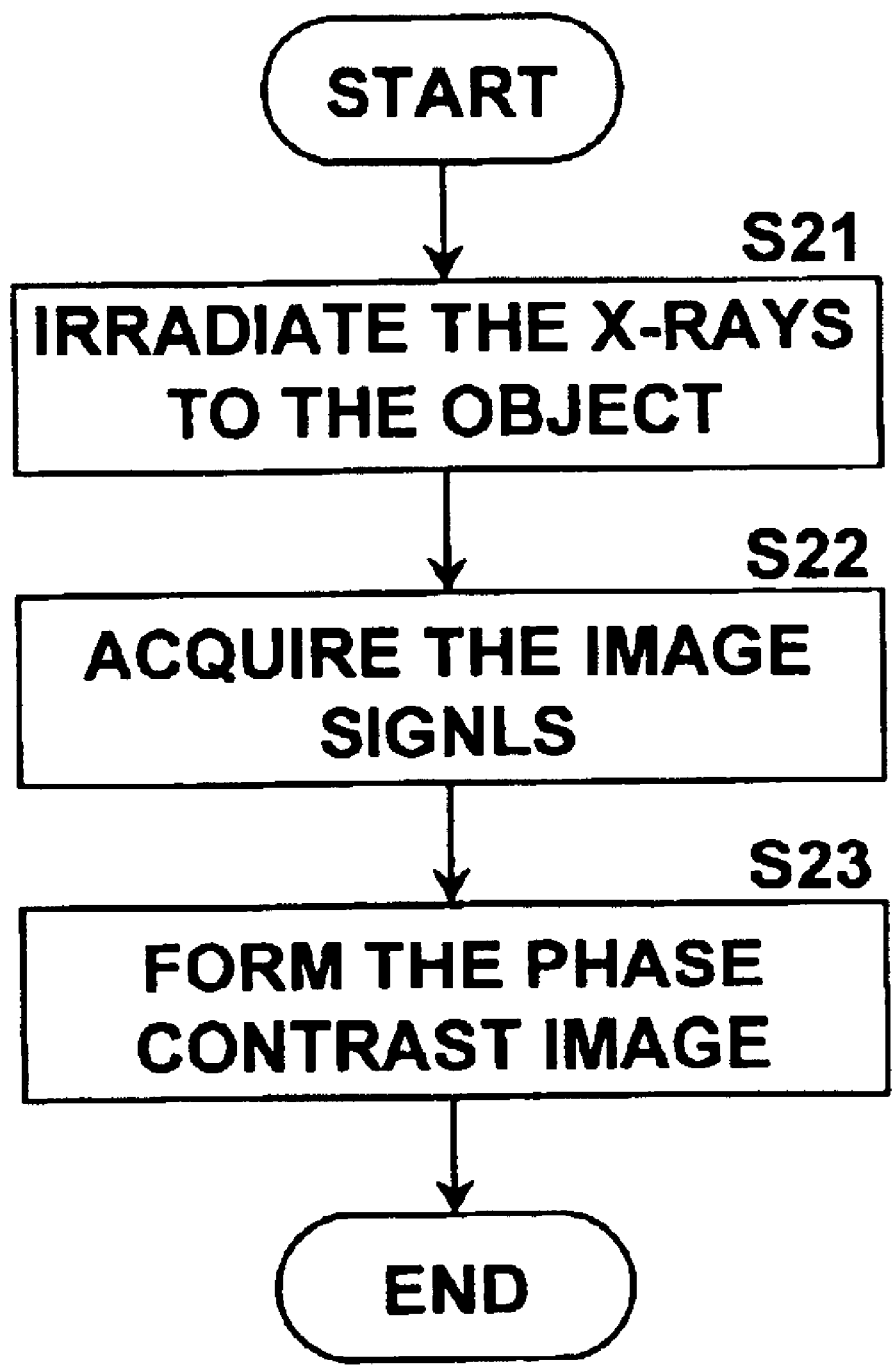
FIG. 9 is a flow chart showing how the fourth embodiment of the radiation image recording apparatus in accordance with the present invention operates.

FIG. 9 is a flow chart showing how the fourth embodiment of the radiation image recording apparatus in accordance with the present invention operates. As illustrated in FIG. 9, firstly, in a step S21, the X-ray beam producing device 11 is actuated to produce the synchrotron radiation beam, and the synchrotron radiation beam is reflected from the crystal 13. In this manner, the monochromatic X-rays 12 are radiated out from the X-ray source 10 and irradiated to the object 21. Also, in a step S22, the electric signal components are read out from the plurality of the detecting devices, which constitute each of the X-ray detecting panels 231, 232, and 233, and with each of the reading means 234, 235, and 236 located at the plurality of the positions for image recording. In this manner, the image signals Sn, each of which represents one of the X-ray images obtained at the plurality of the positions for image recording, are acquired.

In a step S23, the thus acquired image signals Sn are fed into the operation processing section 240. In the operation processing section 240, the image signals Sn are subjected to the compensation for the resolution and the image size enlargement processing. Also, in the manner described above, the image signal Sp representing the phase contrast image is formed from the image signals Sn, which have been obtained from the compensation for the resolution and the image size enlargement processing. At this stage, the processing with the radiation image recording apparatus is finished. The image signal Sp representing the phase contrast image may be utilized for the reproduction of a visible image on a monitor or for the print outputting with a printer.

As described above, in the fourth embodiment, the X-ray images are acquired by use of the X-ray detecting panels 231, 232, and 233 having been set such that the X-ray detecting panel located at the position for image recording, which is remote from the object 21, has a resolution higher than the resolution of the X-ray detecting panel located at the position for image recording, which is close to the object 21. Therefore, the X-ray images are capable of being acquired such that the high-frequency information due to the diffraction image may not be lost. Also, at the position for image recording, which is close to the object 21, the X-ray image having a resolution lower than the resolution of the X-ray image acquired at the position for image recording, which is remote from the object, is obtained. Accordingly, the signal reading from the X-ray detecting panel is capable of being performed efficiently. As a result, the plurality of the X-ray images, from which the phase contrast image is to be formed, are capable of being acquired efficiently, and the phase contrast image is capable of being formed efficiently.

A fifth embodiment of the radiation image recording apparatus in accordance with the present invention will be described hereinbelow.

Figure 10:
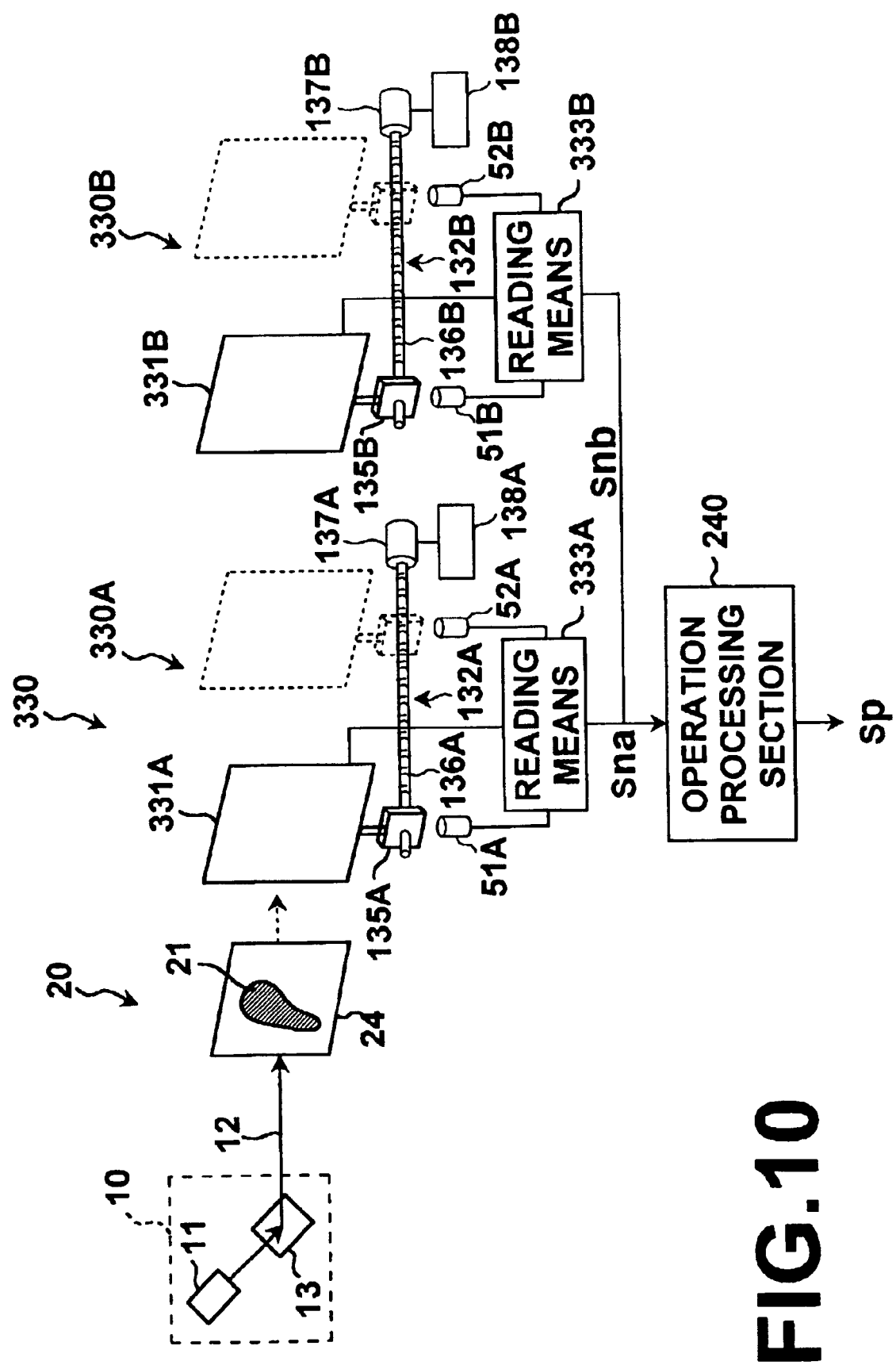
FIG. 10 is a schematic block diagram showing a phase contrast imaging apparatus, in which a fifth embodiment of the radiation image recording apparatus in accordance with the present invention is employed.

FIG. 10 is a schematic block diagram showing a phase contrast imaging apparatus, in which the fifth embodiment of the radiation image recording apparatus in accordance with the present invention is employed. In FIG. 10, similar elements are numbered with the same reference numerals with respect to FIG. 7. The fifth embodiment is constituted basically in the same manner as that for the fourth embodiment, except for the recording section.

In the fifth embodiment, a recording section 330 comprises a first image recording unit 330A and a second image recording unit 330B.

The first image recording unit 330A is provided with an X-ray detecting panel 331A, which comprises a phosphor and a plurality of detecting devices arrayed in two-dimensional directions. The first image recording unit 330A is also provided with the movement means 132A for moving the X-ray detecting panel 331A in parallel with the direction along which the X-rays 12 carrying the image information of the object 21 travels. The first image recording unit 330A is further provided with reading means 333A for reading electric signal components from the plurality of the detecting devices, which constitute the X-ray detecting panel 331A, at each of a plurality of positions for image recording, which have been set previously on the movement path of the X-ray detecting panel 331A. The reading means 333A thus obtains each of a plurality of image signals Sna, which represent the X-ray images recorded at the plurality of the positions for image recording.

Also, the second image recording unit 330B is provided with an X-ray detecting panel 331B, which comprises a phosphor and a plurality of detecting devices arrayed in two-dimensional directions. The second image recording unit 330B is also provided with the movement means 132B for moving the X-ray detecting panel 331B in parallel with the direction along which the X-rays 12 carrying the image information of the object 21 travels. The second image recording unit 330B is further provided with reading means 333B for reading electric signal components from the plurality of the detecting devices, which constitute the X-ray detecting panel 331B, at each of a plurality of positions for image recording, which have been set previously on the movement path of the X-ray detecting panel 331B. The reading means 333B thus obtains each of a plurality of image signals Snb, which represent the X-ray images recorded at the plurality of the positions for image recording.

The movement means 132A is provided with the support member 135A, which supports the X-ray detecting panel 331A and has the internal thread section. The movement means 132A is also provided with the screw rod 136A extending in parallel with the direction along which the X-rays 12 travels. The screw rod 136A has the external threads for engagement with the internal thread section of the support member 135A. The movement means 132A is further provided with the motor 137A for rotating the screw rod 136A around the rotation axis extending in the direction along which the X-rays 12 travels. The movement means 132A is still further provided with the control section 138A for controlling the operation of the motor 137A. The motor 137A is actuated by the control section 138A in order to rotate the screw rod 136A. In accordance with the direction of rotation of the screw rod 136A, the support member 135A is moved in the direction heading towards the object 21 or in the direction heading away from the object 21. As a result, the X-ray detecting panel 331A is moved in the direction heading towards the object 21 or in the direction heading away from the object 21.

Also, the movement means 132B is provided with the support member 135B, which supports the X-ray detecting panel 331B and has the internal thread section. The movement means 132B is also provided with the screw rod 136B extending in parallel with the direction along which the X-rays 12 travels. The screw rod 136B has the external threads for engagement with the internal thread section of the support member 135B. The movement means 132B is further provided with the motor 137B for rotating the screw rod 136B around the rotation axis extending in the direction along which the X-rays 12 travels. The movement means 132B is still further provided with the control section 138B for controlling the operation of the motor 137B. The motor 137B is actuated by the control section 138B in order to rotate the screw rod 136B. In accordance with the direction of rotation of the screw rod 136B, the support member 135B is moved in the direction heading towards the object 21 or in the direction heading away from the object 21. As a result, the X-ray detecting panel 331B is moved in the direction heading towards the object 21 or in the direction heading away from the object 21.

Further, each of the position sensors 51A and 52A is located at one of the positions for image recording in the first image recording unit 330A. Each of the position sensors 51A and 52A detects the arrival of the X-ray detecting panel 331A, which is moved by the movement means 132A, at the corresponding position for image recording. At the time at which the X-ray detecting panel 331A arrives at the corresponding position for image recording, each of the position sensors 51A and 52A outputs the detection signal. The detection signal is fed into the reading means 333A. In accordance with the detection signal, the reading means 333A reads the electric signal components from the plurality of the detecting devices, which constitute the X-ray detecting panel 331A, in order to obtain the image signal Sna, which represents the X-ray image recorded at the position for image recording described above.

Also, each of the position sensors 51B and 52B is located at one of the positions for image recording in the second image recording unit 330B. Each of the position sensors 51B and 52B detects the arrival of the X-ray detecting panel 331B, which is moved by the movement means 132B, at the corresponding position for image recording. At the time at which the X-ray detecting panel 331B arrives at the corresponding position for image recording, each of the position sensors 51B and 52B outputs the detection signal. The detection signal is fed into the reading means 333B. In accordance with the detection signal, the reading means 333B reads the electric signal components from the plurality of the detecting devices, which constitute the X-ray detecting panel 331B, in order to obtain the image signal Snb, which represents the X-ray image recorded at the position for image recording described above.

In the fifth embodiment, the position sensors 51A and 52A are located at the two positions in the first image recording unit 330A. Also, the position sensors 51B and 52B are located at the two positions in the second image recording unit 330B. Therefore, the four image signals Sn (i.e., the image signals S1, S2, S3, and S4) are obtained respectively from the four positions for image recording.

Also, in the fifth embodiment, the X-ray detecting panel 331A and the X-ray detecting panel 331B are set such that the resolution of the X-ray detecting panel 331B, which constitutes the second image recording unit 330B located on the side remote from the object 21, is higher than the resolution of the X-ray detecting panel 331A, which constitutes the first image recording unit 330A located on the side close to the object 21. Specifically, the X-ray detecting panels 331A and 331B are set such that the light receiving area of each of the detecting devices constituting the X-ray detecting panel 331B is smaller than the light receiving area of each of the detecting devices constituting the X-ray detecting panel 331A, and the detecting devices constituting the X-ray detecting panel 331B are arrayed at an array density higher than the array density of the detecting devices constituting the X-ray detecting panel 331A. In this manner, the resolution of the X-ray detecting panel 331B is set to be higher than the resolution of the X-ray detecting panel 331A. Accordingly, at the position for image recording, which is remote from the object 21, the high-frequency information due to the diffraction image contained in the X-rays 12 is capable of being detected accurately.

In the same manner as that for the fourth embodiment described above, the operation processing section 240 compensates for the differences among the resolutions of the X-ray images, which are represented by the image signals Sn. Also, the operation processing section 240 performs the image size enlargement processing on the X-ray images, which are represented by the image signals Sn, such that the sizes of the X-ray images represented by the image signals Sn become identical with the size of the X-ray image represented by the image signal S4 obtained from the position for image recording, which is remotest from the object 21. Further, the operation processing section 240 forms the image signal Sp, which represents the phase contrast image, from the image signals Sn, which have been obtained from the image size enlargement processing.

How the fifth embodiment of the radiation image recording apparatus in accordance with the present invention operates will be described hereinbelow.

Figure 11:
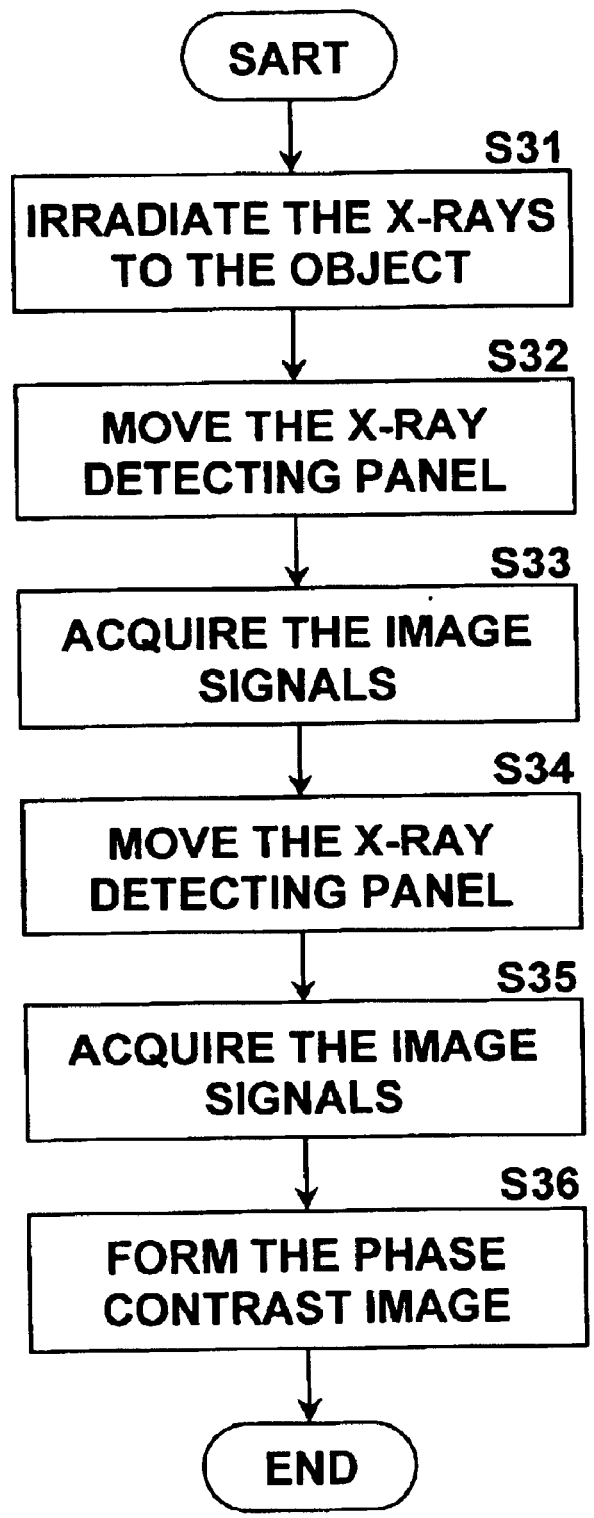
FIG. 11 is a flow chart showing how the fifth embodiment of the radiation image recording apparatus in accordance with the present invention operates.

FIG. 11 is a flow chart showing how the fifth embodiment of the radiation image recording apparatus in accordance with the present invention operates. As illustrated in FIG. 11, firstly, in a step S31, the X-ray beam producing device 11 is actuated to produce the synchrotron radiation beam, and the synchrotron radiation beam is reflected from the crystal 13. In this manner, the monochromatic X-rays 12 are radiated out from the X-ray source 10 and irradiated to the object 21. At the same time, an image recording operation is performed with the first image recording unit 330A. Specifically, in a step S32, the motor 137A is actuated by the control section 138A, and the X-ray detecting panel 331A is moved in the direction heading away from an initial position, which is closest to the object 21. Also, in a step S33, with the timing with which the detection signal is fed from each of the position sensors 51A and 52A into the reading means 333A during the movement of the X-ray detecting panel 331A, the electric signal components are read out from the plurality of the detecting devices, which constitute the X-ray detecting panel 331A, and with the reading means 333A. In this manner, the image signals Sna, each of which represents one of the X-ray images obtained at the positions for image recording, are acquired.

After the image recording operation has been performed at the position for image recording, which is remotest from the object 21, in the first image recording unit 330A, an image recording operation is performed with the second image recording unit 330B. Specifically, in a step S34, the motor 137B is actuated by the control section 138B, and the X-ray detecting panel 331B is moved in the direction heading away from an initial position, which is closest to the object 21. Also, in a step S35, with the timing with which the detection signal is fed from each of the position sensors 51B and 52B into the reading means 333B during the movement of the X-ray detecting panel 331B, the electric signal components are read out from the plurality of the detecting devices, which constitute the X-ray detecting panel 331B, and with the reading means 333B. In this manner, the image signals Snb, each of which represents one of the X-ray images obtained at the positions for image recording, are acquired.

In a step S36, the thus acquired image signals Sna and Snb are fed into the operation processing section 240. In the operation processing section 240, in the same manner as that for the fourth embodiment described above, the image signal Sp representing the phase contrast image is formed from the image signals Sna and Snb. At this stage, the processing with the radiation image recording apparatus is finished. The image signal Sp representing the phase contrast image may be utilized for the reproduction of a visible image on a monitor or for the print outputting with a printer.

In the fifth embodiment described above, after the image recording operation has been performed with the first image recording unit 330A, the image recording operation with the second image recording unit 330B is performed. Alternatively, both the image recording operation with the first image recording unit 330A and the image recording operation with the second image recording unit 330B may be performed simultaneously.

Also, in the fifth embodiment described above, the two image recording units 330A and 330B are utilized. Alternatively, at least three image recording units may be utilized. In such cases, the X-ray detecting panels of the image recording units are set such that an X-ray detecting panel of an image recording unit located on the side remote from the object 21 has a resolution higher than the resolution of an X-ray detecting panel of an image recording unit located on the side close to the object 21.

A sixth embodiment of the radiation image recording apparatus in accordance with the present invention will be described hereinbelow.

Figure 12:
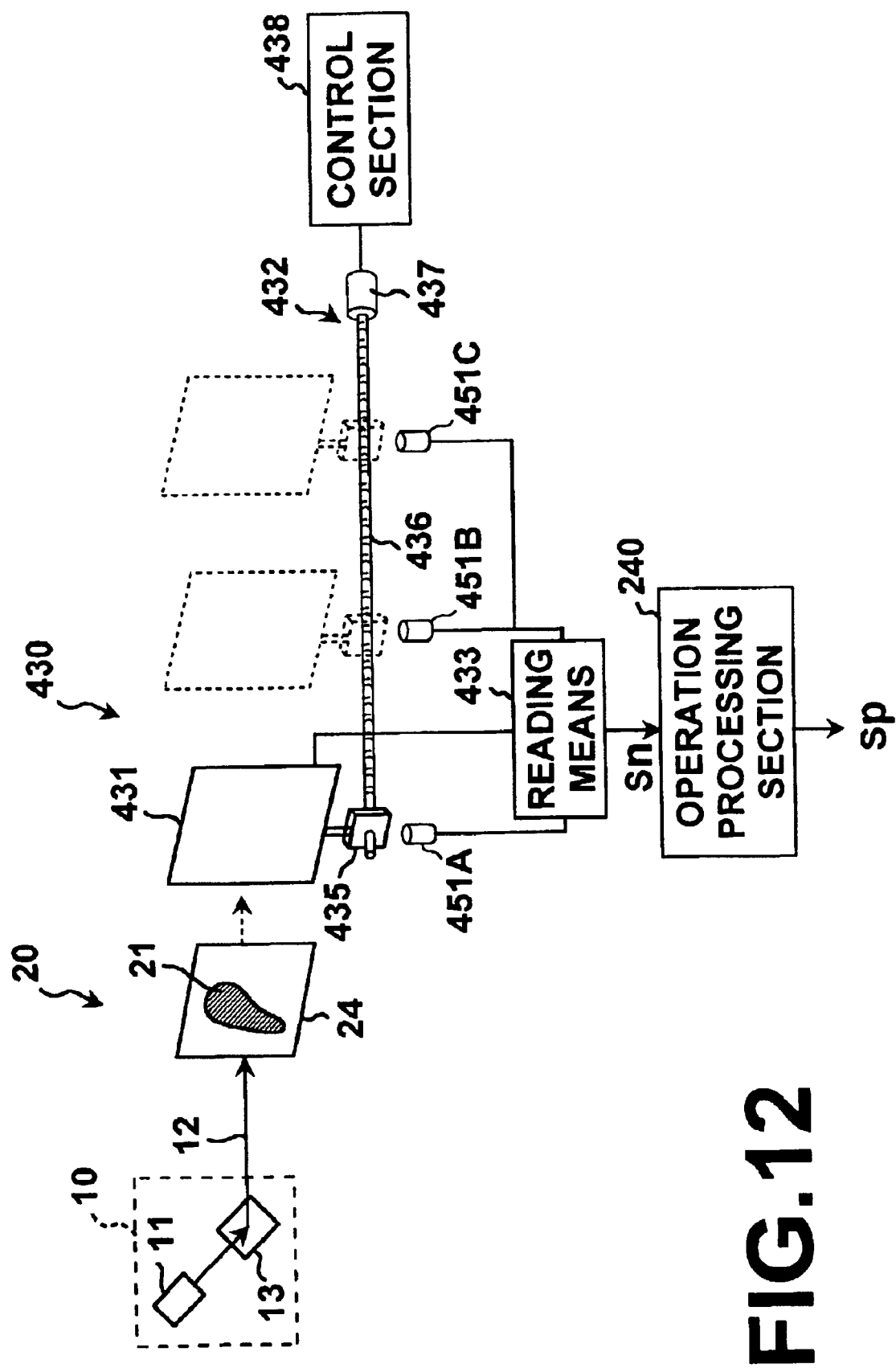
FIG. 12 is a schematic block diagram showing a phase contrast imaging apparatus, in which a sixth embodiment of the radiation image recording apparatus in accordance with the present invention is employed.

FIG. 12 is a schematic block diagram showing a phase contrast imaging apparatus, in which the sixth embodiment of the radiation image recording apparatus in accordance with the present invention is employed. In FIG. 12, similar elements are numbered with the same reference numerals with respect to FIG. 7. The sixth embodiment is constituted basically in the same manner as that for the fourth embodiment, except for the recording section.

In the sixth embodiment, a recording section 430 is provided with an X-ray detecting panel 431, which comprises a phosphor and a plurality of detecting devices arrayed in two-dimensional directions. The recording section 430 is also provided with movement means 432 for moving the X-ray detecting panel 431 in parallel with the direction along which the X-rays 12 carrying the image information of the object 21 travels. The recording section 430 is further provided with reading means 433 for reading electric signal components from the plurality of the detecting devices, which constitute the X-ray detecting panel 431, at each of a plurality of positions for image recording, which have been set previously on the movement path of the X-ray detecting panel 431. The reading means 433 thus obtains each of a plurality of image signals Sn, which represent the X-ray images recorded at the plurality of the positions for image recording.

The movement means 432 is provided with a support member 435, which supports the X-ray detecting panel 431 and has the internal thread section. The movement means 432 is also provided with a screw rod 436 extending in parallel with the direction along which the X-rays 12 travels. The screw rod 436 has the external threads for engagement with the internal thread section of the support member 435. The movement means 432 is further provided with a motor 437 for rotating the screw rod 436 around a rotation axis extending in the direction along which the X-rays 12 travels. The movement means 432 is still further provided with a control section 438 for controlling the operation of the motor 437. The motor 437 is actuated by the control section 438 in order to rotate the screw rod 436. In accordance with the direction of rotation of the screw rod 436, the support member 435 is moved in the direction heading towards the object 21 or in the direction heading away from the object 21. As a result, the X-ray detecting panel 431 is moved in the direction heading towards the object 21 or in the direction heading away from the object 21.

Further, each of position sensors 451A, 451B, and 451C is located at one of the positions for image recording in the recording section 430. Each of the position sensors 451A, 451B, and 451C detects the arrival of the X-ray detecting panel 431, which is moved by the movement means 432, at the corresponding position for image recording. At the time at which the X-ray detecting panel 431 arrives at the corresponding position for image recording, each of the position sensors 451A, 451B, and 451C outputs a detection signal. The detection signal is fed into the reading means 433. In accordance with the detection signal, the reading means 433 reads the electric signal components from the plurality of the detecting devices, which constitute the X-ray detecting panel 431, in order to obtain the image signal Sn, which represents the X-ray image recorded at the position for image recording described above.

The reading means 433 alters the rate of thinning-out of the signal reading from the X-ray detecting panel 431 in accordance with the distances between the positions for image recording and the object 21 and thereby alters the resolutions of the acquired X-ray images.

Figure 13A:
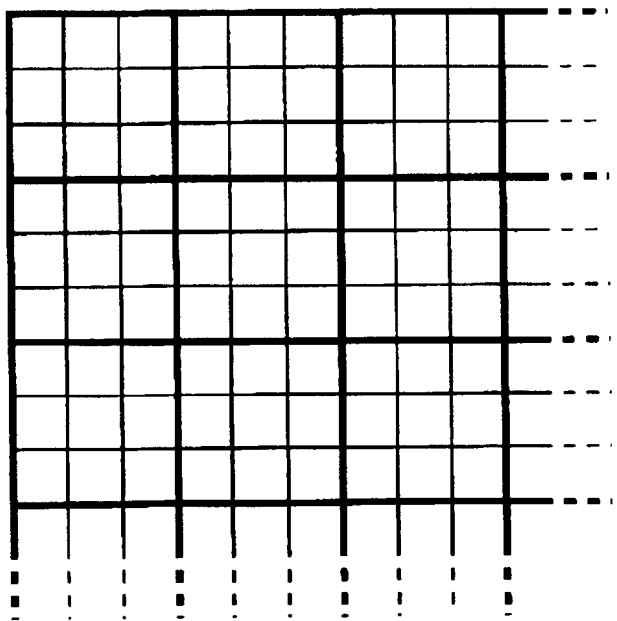
FIG. 13A is an explanatory view showing how a rate of thinning-out of signal reading from a radiation detecting panel is set at the time of acquisition of a radiation image at a position for image recording, which is closest to an object.

Specifically, as illustrated in FIG. 13A, at the time of the signal reading from the X-ray detecting panel 431 located at the position for image recording, which is closest to the object 21, a signal component is read from only one detecting device, which is selected from each set of nine (=3×3) detecting devices adjacent to one another, and the value of the thus read signal component is taken as the pixel values of nine pixels in the X-ray image, which pixels correspond to the nine detecting devices. More specifically, instead of the signal components being read from all of the nine detecting devices, the signal component is read from only one detecting device, which is selected from each set of the nine detecting devices adjacent to one another, and it is regarded that the values of the signal components, which will ordinarily be read from the nine detecting devices, are identical with the value of the signal component, which has been read from the one detecting device. In this manner, the signal reading is thinned out at a high rate of thinning-out, and the signal components representing the X-ray image are obtained.

Figure 13B:
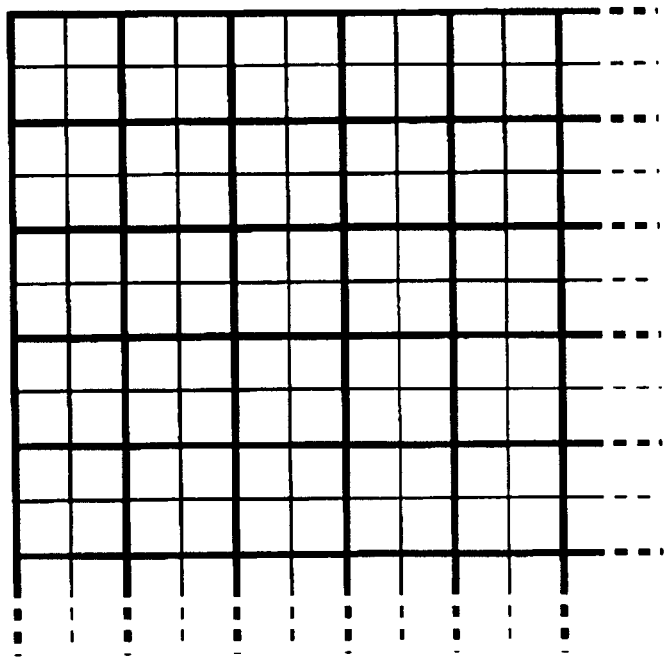
FIG. 13B is an explanatory view showing how the rate of thinning-out of the signal reading from the radiation detecting panel is set at the time of the acquisition of a radiation image at a position for image recording, which is second closest to the object.

Also, as illustrated in FIG. 13B, at the time of the signal reading from the X-ray detecting panel 431 located at the position for image recording, which is second closest to the object 21, a signal component is read from only one detecting device, which is selected from each set of four (=2×2) detecting devices adjacent to one another, and the value of the thus read signal component is taken as the pixel values of four pixels in the X-ray image, which pixels correspond to the four detecting devices. More specifically, instead of the signal components being read from all of the four detecting devices, the signal component is read from only one detecting device, which is selected from each set of the four detecting devices adjacent to one another, and it is regarded that the values of the signal components, which will ordinarily be read from the four detecting devices, are identical with the value of the signal component, which has been read from the one detecting device. In this manner, the signal reading is thinned out at a low rate of thinning-out, and the signal components representing the X-ray image are obtained. Further, at the time of the signal reading from the X-ray detecting panel 431 located at the position for image recording, which is remotest from the object 21, signal components are read from all of the detecting devices constituting the X-ray detecting panel 431, and the signal components representing the X-ray image are obtained.

In the manner described above, in the sixth embodiment, as the distance between the position for image recording and the object 21 becomes long, the rate of thinning-out of the signal reading from the X-ray detecting panel 431 is set to be low. As a result, as the distance between the position for image recording and the object 21 becomes long, the X-ray image having a high resolution is capable of being acquired. Also, at the time of the signal reading from the X-ray detecting panel 431 located at the position for image recording, which is close to the object 21, the rate of thinning-out of the signal reading is set to be higher than the rate of thinning-out of the signal reading from the X-ray detecting panel 431 located at the position for image recording, which is remote from the object 21. Therefore, the signal reading from the X-ray detecting panel 431 is capable of being performed efficiently. As a result, the plurality of the X-ray images are capable of being acquired efficiently, and the phase contrast image is capable of being formed efficiently from the plurality of the X-ray images.

Figure 14:
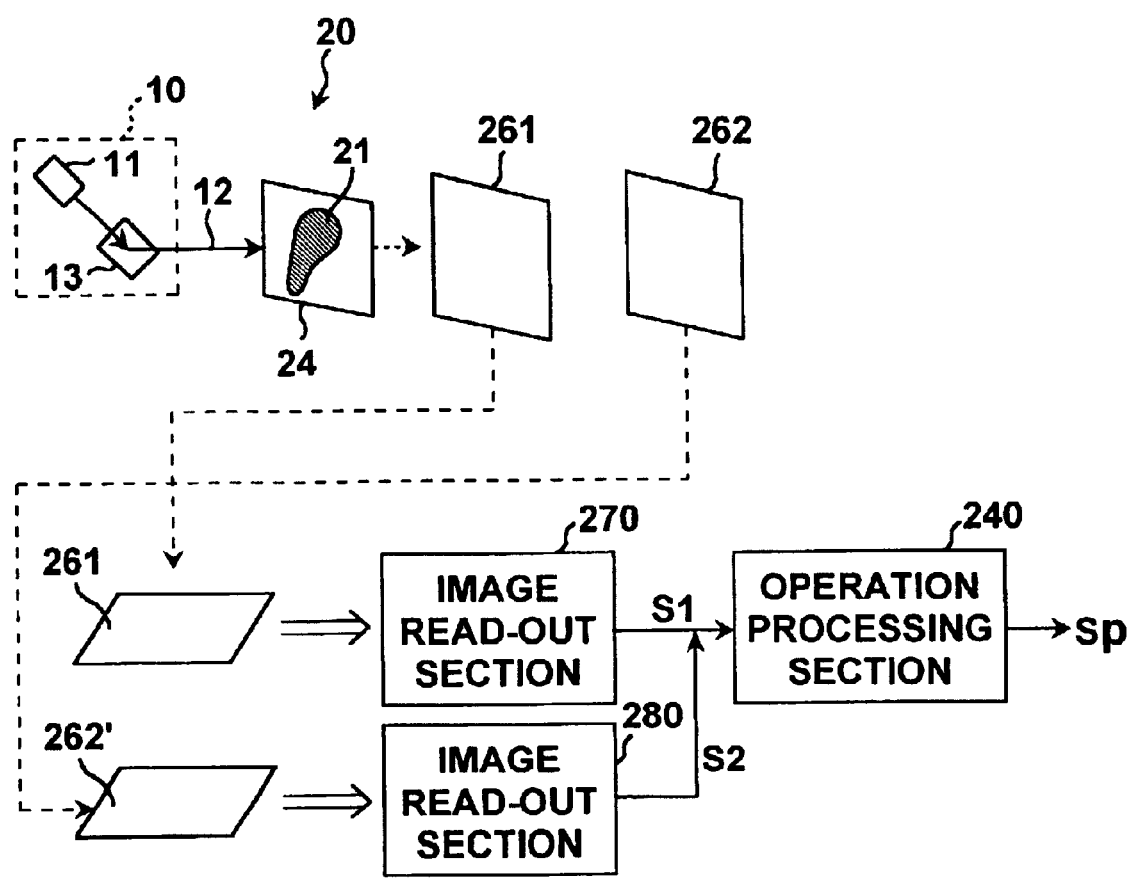
FIG. 14 is a schematic block diagram showing a phase contrast imaging apparatus, in which a seventh embodiment of the radiation image recording apparatus in accordance with the present invention is employed.

In the fourth embodiment shown in FIG. 7, the X-ray images are acquired with the X-ray detecting panels 231, 232, and 233. Alternatively, as in a seventh embodiment illustrated in FIG. 14, in lieu of the X-ray detecting panels 231, 232, and 233, a stimulable phosphor sheet 261 and X-ray film 262 may be utilized. The X-ray film 262 is capable of yielding an X-ray image, which has better graininess characteristics and therefore has a higher resolution than with the stimulable phosphor sheet 261.

In cases where the X-ray image has been recorded on the stimulable phosphor sheet 261, the stimulable phosphor sheet 261, on which the X-ray image has been stored, is sent to an image read-out section 270. In the image read-out section 270, the stimulable phosphor sheet 261, on which the X-ray image has been stored, is exposed to the stimulating rays, which cause the stimulable phosphor sheet to emit light in proportion to the amount of energy stored thereon during its exposure to the X-rays 12. Also, the light emitted by the stimulable phosphor sheet 261 is photoelectrically detected. In this manner, the image signal S1, which represents the X-ray image having been stored on the stimulable phosphor sheet 261, is obtained.

In cases where the X-ray image has been recorded on the X-ray film 262, the X-ray film 262, on which the X-ray image has been recorded, is subjected to a development process. Also, developed X-ray film 262' is sent to an image read-out section 280, which is capable of reading an image from X-ray film. In the image read-out section 280, the X-ray image is read out from the developed X-ray film 262', and the image signal S2 representing the X-ray image having been recorded on the X-ray film 262 is obtained.

In the same manner as that for the fourth embodiment described above, the thus obtained image signals S1 and S2 are fed into the operation processing section 240. In the operation processing section 240, the image signal Sp representing the phase contrast image is formed from the image signals S1 and S2.

In the first to seventh embodiments described above, the X-ray beam producing device 11, which produces the synchrotron radiation beam, is utilized. However, one of various other types of X-ray beam producing devices may be utilized as the X-ray beam producing device 11. Also, in the first to seventh embodiments described above, the monochromatic X-rays are utilized as the X-rays 12 irradiated to the object 21. However, the X-rays 12 are not limited to the monochromatic X-rays.

Further, in the first to seventh embodiments described above, the X-rays 12 are irradiated to the object 21. Alternatively, in lieu of the X-rays, other radiation (alpha-rays, beta-rays, gamma-rays, cathode rays, or the like) may be utilized.

What is claimed is:

1. A radiation image recording method, comprising the steps of:

i) irradiating radiation to an object, and ii) detecting the radiation, which carries image information of the object, at a plurality of positions for image recording, which are set at different distances from the object, a plurality of radiation images of the object being thereby acquired, wherein the acquisition of the plurality of the radiation images of the object is performed by use of a plurality of two-dimensional detectors, such that the radiation, which carries the image information of the object, at a position for image recording, which is remote from the object, is detected with a two-dimensional detector having a sensitivity higher than the sensitivity of a two-dimensional detector for detecting the radiation at a position for image recording, which is close to the object, and wherein the radiation is at least one of: x-rays, alpha-rays, beta-rays, gamma-rays and cathode rays.

2. A method as defined in claim 1 wherein a two-dimensional detector for detecting the radiation at a position for image recording, which is close to the object, has a radiation transmittance higher than the radiation transmittance of a two-dimensional detector for detecting the radiation at a position for image recording, which is remote from the object.

3. A method as defined in claim 1 or 2 wherein a phase contrast image is formed from the plurality of the radiation images.

4. A radiation image recording apparatus, comprising:

a plurality of two-dimensional detectors, each of the two-dimensional detectors being located at one of a plurality of positions for image recording, which are set at different distances from an object, in order to detect radiation, which carries image information of the object, at the one position for image recording, the plurality of the two-dimensional detectors being set such that a two-dimensional detector located at a position for image recording, which is remote from the object, has a sensitivity higher than the sensitivity of a two-dimensional detector located at a position for image recording, which is close to the object, wherein the radiation, which carries the image information of the object, is detected with the plurality of the two-dimensional detectors at the plurality of the positions for image recording, a plurality of radiation images of the object being thereby acquired and wherein the radiation is at least one of: x-rays, alpha-rays, beta-rays, gamma-rays and cathode rays.

5. An apparatus as defined in claim 4 wherein the plurality of the two-dimensional detectors are set such that a two-dimensional detector located at a position for image recording, which is close to the object, has a radiation transmittance higher than the radiation transmittance of a two-dimensional detector located at a position for image recording, which is remote from the object.

6. An apparatus as defined in claim 4 or 5 wherein the apparatus further comprises image forming means for forming a phase contrast image from the plurality of the radiation images.

7. A radiation image recording apparatus, comprising:
i) a plurality of image recording units located successively along a direction of an optical axis of radiation, which carries image information of an object, each of the image recording units comprising:
  a two-dimensional detector for detecting the radiation, which carries the image information of the object,
  movement means for moving the two-dimensional detector in the direction of the optical axis of the radiation, and
  a plurality of position sensors, each of the position sensors detecting arrival of the two-dimensional detector at one of a plurality of positions for image recording, which have been predetermined on a movement path of the two-dimensional detector moved by the movement means, and
ii) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording, wherein a plurality of the two-dimensional detectors of the plurality of the image recording units are set such that a two-dimensional detector of an image recording unit, which is located at a position remote from the object, has a sensitivity higher than the sensitivity of a two-dimensional detector of an image recording unit, which is located at a position close to the object, and wherein the radiation is at least one of: x-rays, alpha-rays, beta-rays, gamma-rays and cathode rays.

8. An apparatus as defined in claim 7 wherein the apparatus comprises a plurality of reading means, each of which is located for one of the plurality of the image recording units.

9. An apparatus as defined in claim 7 or 8 wherein the plurality of the two-dimensional detectors of the plurality of the image recording units are set such that a two-dimensional detector of an image recording unit, which is located at a position close to the object, has a radiation transmittance higher than the radiation transmittance of a two-dimensional detector of an image recording unit, which is located at a position remote from the object.

10. An apparatus as defined in claim 7 or 8 wherein the apparatus further comprises image forming means for forming a phase contrast image from the plurality of the radiation images.

11. A radiation image recording method, comprising the steps of:
i) irradiating radiation to an object, and
ii) detecting the radiation, which carries image information of the object, at a plurality of positions for image recording, which are set at different distances from the object, a plurality of radiation images of the object being thereby acquired, wherein the acquisition of the plurality of the radiation images of the object is performed such that a resolution of a radiation image acquired at a position for image recording, which is remote from the object, becomes higher than the resolution of a radiation image acquired at a position for image recording, which is close to the object, and wherein the radiation is at least one of: x-rays, alpha-rays, beta-rays, gamma-rays and cathode rays.

12. A method as defined in claim 11 wherein the acquisition of the plurality of the radiation images of the object is performed by use of a plurality of two-dimensional detectors, such that the radiation, which carries the image information of the object, at a position for image recording, which is remote from the object, is detected with a two-dimensional detector having a resolution higher than the resolution of a two-dimensional detector for detecting the radiation at a position for image recording, which is close to the object.

13. A method as defined in claim 11 wherein the acquisition of the plurality of the radiation images of the object is performed by use of at least one two-dimensional detector, such that a rate of thinning-out of signal reading from the two-dimensional detector at the time of the acquisition of a radiation image at a position for image recording, which is remote from the object, is lower than the rate of thinning-out of the signal reading from the two-dimensional detector at the time of the acquisition of a radiation image at a position for image recording, which is close to the object.

14. A method as defined in claim 11, 12, or 13 wherein a phase contrast image is formed from the plurality of the radiation images.

15. A radiation image recording apparatus, comprising:
a plurality of two-dimensional detectors, each of the two-dimensional detectors being located at one of a plurality of positions for image recording, which are set at different distances from an object, in order to detect radiation, which carries image information of the object, at the one position for image recording, the plurality of the two-dimensional detectors being set such that a two-dimensional detector located at a position for image recording, which is remote from the object, has a resolution higher than the resolution of a two-dimensional detector located at a position for image recording, which is close to the object, wherein the radiation, which carries the image information of the object, is detected with the plurality of the two-dimensional detectors at the plurality of the positions for image recording, a plurality of radiation images of the object being thereby acquired and wherein the radiation is at least one of: x-rays, alpha-rays, beta-rays, gamma-rays and cathode rays.

16. An apparatus as defined in claim 15 wherein the apparatus further comprises image forming means for forming a phase contrast image from the plurality of the radiation images.

17. A radiation image recording apparatus, comprising:
i) a plurality of image recording units located successively along a direction of an optical axis of radiation, which carries image information of an object, each of the image recording units comprising:
a two-dimensional detector for detecting the radiation, which carries the image information of the object,
movement means for moving the two-dimensional detector in the direction of the optical axis of the radiation, and
a plurality of position sensors, each of the position sensors detecting arrival of the two-dimensional detector at one of a plurality of positions for image recording, which have been predetermined on a movement path of the two-dimensional detector moved by the movement means, and
ii) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording,
wherein a plurality of the two-dimensional detectors of the plurality of the image recording units are set such that a two-dimensional detector of an image recording unit, which is located at a position remote from the object, has a resolution higher than the resolution of a two-dimensional detector of an image recording unit, which is located at a position close to the object, and
wherein the radiation is at least one of: x-rays, alpha-rays, beta-rays, gamma-rays and cathode rays.

18. An apparatus as defined in claim 17 wherein the apparatus comprises a plurality of reading means, each of which is located for one of the plurality of the image recording units.

19. An apparatus as defined in claim 17 or 18 wherein the apparatus further comprises image forming means for forming a phase contrast image from the plurality of the radiation images.

20. A radiation image recording apparatus, comprising:
i) at least one two-dimensional detector for detecting radiation, which carries image information of an object,
ii) movement means for moving the two-dimensional detector in a direction of an optical axis of the radiation,
iii) a plurality of position sensors, each of the position sensors detecting arrival of the two-dimensional detector at one of a plurality of positions for image recording, which have been predetermined on a movement path of the two-dimensional detector moved by the movement means, and
iv) reading means for operating in accordance with results of the detection obtained from each of the position sensors such that, when the two-dimensional detector has arrived at one of the positions for image recording, the reading means reads a signal from the two-dimensional detector in order to acquire a radiation image of the object, a plurality of radiation images of the object being acquired with respect to the plurality of the positions for image recording,
the reading means performing the reading of signals from the two-dimensional detector such that a rate of thinning-out of signal reading from the two-dimensional detector at the time of the acquisition of a radiation image at a position for image recording, which is remote from the object, is lower than the rate of thinning-out of the signal reading from the two-dimensional detector at the time of the acquisition of a radiation image at a position for image recording, which is close to the objects
wherein the radiation is at least one of: x-rays, alpha-rays, beta-rays, gamma-rays and cathode rays.

21. An apparatus as defined in claim 20 wherein the apparatus further comprises image forming means for forming a phase contrast image from the plurality of the radiation images.

* * * * *